US009994680B2

(12) United States Patent
Hayashi et al.

(10) Patent No.: US 9,994,680 B2
(45) **Date of Patent: *Jun. 12, 2018**

(54) CO-MODIFIED ORGANOPOLYSILOXANE, AND TREATMENT AGENT AND EXTERNAL USE PREPARATION COMPRISING THE SAME

(71) Applicant: Dow Corning Toray Co., Ltd., Tokyo (JP)

(72) Inventors: Akito Hayashi, Ichihara (JP); Tomohiro Iimura, Ichihara (JP); Tatsuo Souda, Ichihara (JP); Seiki Tamura, Ichihara (JP); Haruhiko Furukawa, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/369,247

(22) PCT Filed: Dec. 26, 2012

(86) PCT No.: PCT/JP2012/084280

§ 371 (c)(1),
(2) Date: Jun. 27, 2014

(87) PCT Pub. No.: WO2013/100177

PCT Pub. Date: Jul. 4, 2013

(65) Prior Publication Data

US 2014/0371330 A1 Dec. 18, 2014

(30) Foreign Application Priority Data

Dec. 27, 2011 (JP) ................................ 2011-286973

(51) Int. Cl.

| | |
|---|---|
| ***C08G 77/18*** | (2006.01) |
| ***C08G 77/38*** | (2006.01) |
| ***C08G 77/46*** | (2006.01) |
| ***C08G 77/50*** | (2006.01) |
| ***A61Q 1/02*** | (2006.01) |
| ***A61K 8/894*** | (2006.01) |
| ***A61K 8/06*** | (2006.01) |
| ***A61K 8/02*** | (2006.01) |
| ***A61Q 1/00*** | (2006.01) |
| *A61Q 17/04* | (2006.01) |
| *A61Q 19/00* | (2006.01) |
| *A61Q 1/04* | (2006.01) |
| *A61Q 1/06* | (2006.01) |
| *A61Q 1/10* | (2006.01) |

(52) U.S. Cl.

CPC .............. *C08G 77/18* (2013.01); *A61K 8/022* (2013.01); *A61K 8/064* (2013.01); *A61K 8/894* (2013.01); *A61Q 1/00* (2013.01); *A61Q 1/02* (2013.01); *C08G 77/38* (2013.01); *C08G 77/46* (2013.01); *C08G 77/50* (2013.01); *A61K 2800/10* (2013.01); *A61Q 1/04* (2013.01); *A61Q 1/06* (2013.01); *A61Q 1/10* (2013.01); *A61Q 17/04* (2013.01); *A61Q 19/00* (2013.01)

(58) Field of Classification Search

USPC ................................ 556/430, 445, 449, 450

See application file for complete search history.

(56) References Cited

U.S. PATENT DOCUMENTS

| | | | | |
|---|---|---|---|---|
| 9,133,309 B2 * | 9/2015 | Iimura | .................. | A61Q 19/00 |
| 2003/0185771 A1 | 10/2003 | Kamei et al. | | |
| 2012/0269747 A1 * | 10/2012 | Iimura | .................. | A61Q 19/00 424/59 |
| 2012/0269875 A1 | 10/2012 | Tamura et al. | | |
| 2014/0004065 A1 | 1/2014 | Souda et al. | | |

FOREIGN PATENT DOCUMENTS

| | | |
|---|---|---|
| EP | 2492300 A1 | 8/2012 |
| JP | H0753326 A | 2/1995 |
| JP | H10167946 A | 6/1998 |
| JP | 2002038013 A | 2/2002 |
| JP | 2010289722 | 12/2010 |
| JP | 2012246445 A | 12/2012 |

(Continued)

OTHER PUBLICATIONS

English language abstract and machine-assisted English translation for JPH0753326 extracted from espacenet.com database on Sep. 15, 2014, 11 pages.

English language abstract and machine-assisted English translation for JPH10167946 extracted from espacenet.com database on Sep. 15, 2014, 10 pages.

English language abstract for JP2002038013 extracted from espacenet.com database on Sep. 15, 2014, 2 pages. Also see English equivalent US 2003/0185771.

English language abstract and machine-assisted English translation for JP2012246445 extracted from espacenet.com database on Sep. 15, 2014, 29 pages.

English language abstract for WO2011049246 extracted from espacenet.com database on Sep. 8, 2014, 2 pages. Also see English equivalent EP2492300.

(Continued)

*Primary Examiner* — Pancham Bakshi

(74) *Attorney, Agent, or Firm* — Howard & Howard Attorneys PLLC

(57) ABSTRACT

A co-modified organopolysiloxane having a viscosity at 25° C. of not more than 1,500 mPa·s, a group that has a siloxane dendron structure, a hydrophilic group, and expressed by the following general formula (1): $R^1{}_aR^2{}_bL^1{}_cQ_dSiO_{(4-a-b-c-d)/2}$ (1). The invention also relates to a powder treatment agent, a powder in oil dispersion, an external use preparation (particularly a cosmetic composition) composition comprising the co-modified organopolysiloxane. In said general formula (1), $R^1$ is a monovalent hydrocarbon group or a hydrogen atom; $R^2$ is a monovalent hydrocarbon group having from 6 to 30 carbons; $L^1$ is a silylalkyl group having a siloxane dendron structure; and Q is a hydrophilic segment.

16 Claims, No Drawings

(56) References Cited

FOREIGN PATENT DOCUMENTS

| | | | |
|---|---|---|---|
| WO | WO2007109240 | A2 | 9/2007 |
| WO | WO2009006091 | A2 | 1/2009 |
| WO | WO2011028765 | A1 | 3/2011 |
| WO | WO2011028770 | A1 | 3/2011 |
| WO | WO2011049246 | A1 | 4/2011 |
| WO | WO2011049248 | A1 | 4/2011 |
| WO | WO2011136394 | A1 | 11/2011 |

OTHER PUBLICATIONS

English language abstract for WO2011049248 extracted from espacenet.com database on Sep. 8, 2014, 2 pages. Also see English equivalent US 2012/0269875.

International Search Report for PCT/JP2012/084280 dated Jun. 20, 2013, 3 pages.

English language abstract for JP2010289722 extracted from espacenet.com database on Nov. 19, 2014, 1 page. Also see US Publication No. 2014/0004065 for English equivalent.

* cited by examiner

CO-MODIFIED ORGANOPOLYSILOXANE, AND TREATMENT AGENT AND EXTERNAL USE PREPARATION COMPRISING THE SAME

CROSS-REFERENCE TO RELATED APPLICATIONS

This application is the National Stage of International Patent Application No. PCT/JP2012/084280, filed on Dec. 26, 2012, which claims priority to and all the advantages of Japanese Patent Application No. 2011-286973, filed on Dec. 27, 2011, the content of which is incorporated herein by reference.

TECHNICAL FIELD

The present invention relates to a novel co-modified organopolysiloxane copolymer that has low viscosity and low molecular weight while having a group that has a carbosiloxy dendron structure and a glycerin derivative, a sugar alcohol, or a similar hydrophilic group in the molecule; and a surfactant or a surface treatment agent, particularly a powder treatment agent, comprising the novel co-modified organopolysiloxane copolymer. Additionally, the present invention relates to a powder that is surface treated using the powder treatment agent, a powder composition comprising the co-modified organopolysiloxane copolymer, and a powder in oil dispersion comprising an oil agent; and, moreover an external use preparation, particularly a make-up cosmetic composition, comprising the same.

BACKGROUND ART

Various powders exemplified by white and colored pigments such as titanium oxide, zinc oxide, red iron oxide, and the like and extender pigments such as mica, sericite, and the like are widely used in the fields of basic cosmetic compositions and other various cosmetic compositions such as sunscreens, nail colors, nail coats, foundations, mascaras, eye liners, and the like. However, untreated powder is prone to agglomerate due to the electric charge and polarity, trace amount of impurities, and the like on the powder surface. Therefore, powders that have been subject to various surface treatments are widely used for the purpose of enhancing dispersibility and stability of a powder in a cosmetic composition and also improving the tactile sensation, moisture resistance, sebum resistance, and the like of a cosmetic composition comprising a powder.

Known examples of such surface treatments include lipophilization treatments using an oil agent, a metal soap, or the like; hydrophilization treatments using a surfactant, water-soluble polymer, or the like; hydrophobization treatments using silicone compounds; silica treatments; alumina treatments; and the like. Particularly, in recent years, there have been many cases where a surface treatment using a silicone compound having a reactive moiety in the molecule have been performed. The reactive moiety forms a chemical bond with the powder surface and, as a result, the surface treatment using the silicone compound is effective from the perspective of simultaneously modifying the surface of the powder and blocking the surface activity of the powder. Additionally, because surface treatment can be thoroughly performed, the surface treatment agent will not separate from the powder surface, even when compounded in a cosmetic composition comprising a solvent. Moreover, changes in properties of the powder due to the surface treatment can be kept to a minimum. An example of such a surface treatment is a method in which a powder is surface treated using a methylhydrogenpolysiloxane (Patent Document 1). However, in this method, unreacted Si—H groups still remain even after the surface treating of the powder and, therefore, there is a problem when this powder is compounded in a cosmetic composition because hydrogen gas may be produced depending on the components and the like in the cosmetic composition.

On the other hand, methods for manufacturing a powder dispersion using a hydrophilic group-modified organopolysiloxane that has good compatibility with the powder surface. Examples thereof include a method for forming a polyether-modified organopolysiloxane into a powder dispersing aid (Patent Document 2) and a method for forming an organopolysiloxane modified by polyglycerine or a similar polyhydric alcohol into a powder dispersing aid (Patent Document 3). However, there are problems in that the powder dispersion effectiveness is still insufficient, viscosity of a power dispersion obtained by dispersing a powder in silicone oil or a similar oil agent increases gradually over time, fluidity is lost, and the like.

As a method to resolve the problems described above, the present applicant has proposed methods using a co-modified organopolysiloxane copolymer having a group that has a carbosiloxy dendron structure and a glycerin derivative, polyhydric alcohol, or similar hydrophilic group in the molecule (Patent Documents 4, 5, and 6). Such co-modified organopolysiloxanes are safe and do not produce hydrogen, and can be advantageously used in the surface treating of a powder. Moreover, affinity with other raw materials of cosmetic compositions is superior, and the dispersibility and stability of the powder in a cosmetic composition comprising a powder can be enhanced.

However, the co-modified organopolysiloxane copolymers described in Patent Documents 4 to 6 have a large content of hydrophilic groups and many hydroxyl groups, and the viscosity of the copolymer itself tend to increase due to cohesive force resulting from hydrogen bonding. Thus, performance is insufficient from the perspective of handling/workability in cases when used as a powder treatment agent. Additionally, efficiency tends to decline when fabricating a dispersion and, thus, the performance of these co-modified organopolysiloxane copolymers is insufficient from the perspective of the dispersibility of powder.

PRIOR ART DOCUMENTS

Patent Documents

Patent Document 1: Japanese Unexamined Patent Application Publication No. H07-53326 (Japanese Patent No. 2719303)

Patent Document 2: Japanese Unexamined Patent Application Publication No. H10-167946

Patent Document 3: Japanese Unexamined Patent Application Publication No. 2002-038013

Patent Document 4: WO2011/049246

Patent Document 5: WO2011/049248

Patent Document 6: International Patent Application No. PCT/JP2011/060800

DISCLOSURE OF THE INVENTION

Technical Problem

A first object of the present invention is to provide a novel co-modified organopolysiloxane by which the problems described above can be resolved. More specifically, a first object of the present invention is to provide a co-modified organopolysiloxane that can advantageously be used as a raw material which, compared to conventional co-modified silicones, has superior workability, superior dispersion fabrication efficiency, and superior powder dispersibility; and has superior compatibility with a wide range of cosmetic raw materials. A second object of the present invention is to provide a powder treatment agent comprising the organopolysiloxane, a powder that is surface treated using the powder treatment agent, a powder composition comprising the co-modified organopolysiloxane copolymer, and a powder in oil dispersion comprising an oil agent; and, moreover an external use preparation, particularly a make-up cosmetic composition, comprising the same.

Solution to Problem

As a result of intensive investigation aimed at achieving the above objects, the present inventors arrived at the present invention. That is, the first object of the present invention is achieved by a novel low viscosity co-modified organopolysiloxane having a group that has a carbosiloxy dendron structure and a glycerin derivative or similar hydrophilic group in the molecule. Additionally, the first object of the present invention is particularly achieved by the co-modified organopolysiloxane described above in which a content of the hydrophilic groups is such that an overall HLB value is not greater than 2, and that has a low degree of polymerization, a low viscosity, and a low HLB; and furthermore optionally has a long chain hydrocarbon group.

Additionally, the second object of the present invention is achieved by a surfactant or a surface treatment agent, particularly a powder treatment agent, comprising the co-modified organopolysiloxane described above. Furthermore, the second object of the present invention is achieved by a powder that is surface treated using the powder treatment agent, a powder composition comprising the co-modified organopolysiloxane copolymer, and a powder in oil dispersion comprising an oil agent; and, moreover an external use preparation, particularly a make-up cosmetic composition, comprising the same.

Specifically, the objects of the present invention are achieved by:

[1] A co-modified organopolysiloxane having a viscosity at 25° C. of not more than 1,500 mPa·s, a group that has a siloxane dendron structure, a hydrophilic group, and expressed by the following general formula (1).

$$R^1_aR^2_bL^1_cQ_dSiO_{(4-a-b-c-d)/2} \qquad (1)$$

In this general formula (1), $R^1$ is a substituted or unsubstituted monovalent hydrocarbon group having from 1 to 30 carbons, or a hydrogen atom; $R^2$ is a substituted or unsubstituted straight or branched monovalent hydrocarbon group having from 6 to 30 carbons; $L^1$ is a silylalkyl group having a siloxane dendron structure expressed by the following general formula (2) when i=1; and Q is a hydrophilic segment.

General Formula (2)

(2)

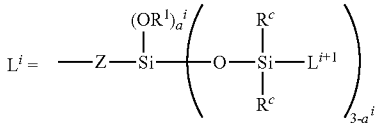

In this general formula (2), $R^1$ is a group synonymous with the groups described above, $R^C$ is an alkyl group having 1 to 6 carbons or a phenyl group, and Z is a divalent organic group; i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c; and $a^i$ is a number in a range of 0 to 3; and a, b, c, and d are numbers in ranges so that $1.0 \leq a+b \leq 2.5$, $0.001 \leq c \leq 1.5$, and $0.001 \leq d \leq 1.5$.

[2] The co-modified organopolysiloxane described in 1, wherein an HLB value calculated by formula (A) below is not more than 2.0.

$$HLB=(\text{total molecular weight of hydrophilic group moiety/total molecular weight})\times 20 \qquad (A)$$

[3] The co-modified organopolysiloxane described in [1] or [2], that is represented by structural formula (1-1) below.

(1-1)

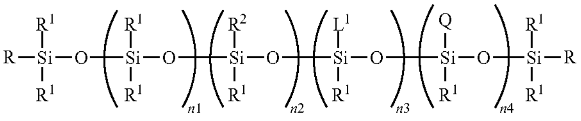

In this formula, $R^1$, $R^2$, $L^1$ and Q are groups synonymous with the groups described above, and R is a group selected from $R^1$, $R^2$, $L^1$, and Q; however, when n3=0, at least one R is $L^1$; and when n4=0, at least one R is Q; and (n1+n2+n3+n4) is a number in a range from 2 to 80; n1 is a number in a range from 0 to 70, n2 is a number in a range from 0 to 30, n3 is a number in a range from 1 to 20, and n4 is a number in a range from 0.1 to 2.

[4] The co-modified organopolysiloxane described in any one of [1] to [3], that is represented by structural formula (1-1-1) below.

(1-1-1)

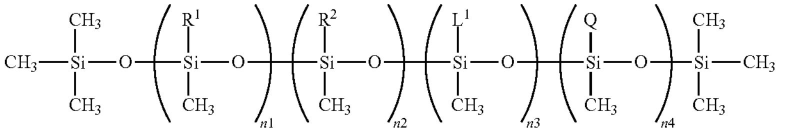

In this formula, $R^1$, $R^2$, $L^1$, and Q are groups synonymous with the groups described above, (n1+n2+n3+n4) is a number in a range from 2 to 80, n1 is a number in a range from 0 to 70, n2 is a number in a range from 0 to 30, n3 is a number in a range from 1 to 20, and n4 is a number in a range from 0.1 to 2.

[5] The co-modified organopolysiloxane described in any one of [1] to [4], wherein in the formulae (1) to (1-1-1), $L^1$ is a functional group expressed by general formula (2-1) or general formula (2-2) below.

General Formula (2-1)

(2-1)

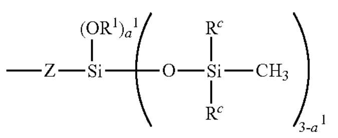

General Formula (2-2):

(2-2)

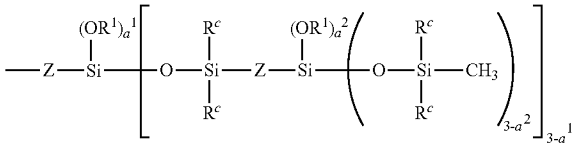

In these formulae, $R^1$, $R^C$, and Z are groups synonymous with the groups described above, and $a^1$ and $a^2$ are each independently numbers in a range of 0 to 3.

[6] The co-modified organopolysiloxane described in any one of [1] to [5], wherein in the formulae (1) to (1-1-1), Q is: a hydrophilic group that is bonded to the silicon atom via a linking group that is at least divalent, comprising a sugar alcohol represented by structural formulae (3-1) and (3-2) below, or a hydrophilic group that is bonded to the silicon atom via a linking group that is at least divalent, comprising at least one hydrophilic unit selected from hydrophilic units represented by structural formulae (3-3) to (3-6) below.

Structural formulae (3-1) and (3-2):

(3-1)

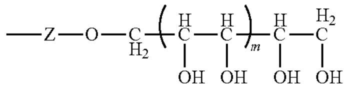

In this formula, Z is a divalent organic group, and m is 1 or 2;

(3-2)

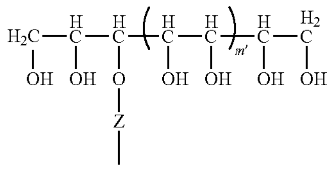

In this formula, Z is synonymous with that described above, and m' is 0 or 1;

Structural formulae (3-3) to (3-6):

$$-C_rH_{2r}-O- \quad (3\text{-}3)$$

In this formula, r is a number in a range of 1 to 6;

(3-4)

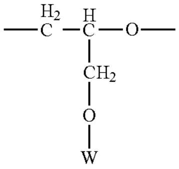

In this formula, W is a hydrogen atom or an alkyl group having from 1 to 20 carbons;

(3-5)

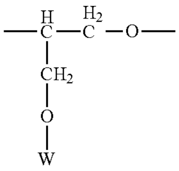

In this formula, W is a group synonymous with the group described above;

(3-6)

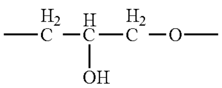

[7] The co-modified organopolysiloxane described in any one of [1] to [6], wherein in the general formulae (1) to (1-1-1), Q is a hydrophilic segment bonded to the silicon atom via a linking group that is at least divalent, comprising at least one linearly bonded hydrophilic unit selected from hydrophilic units represented by structural formulae (3-3) to (3-6) below; or Q is a hydrophilic group bonded to the silicon atom via a linking group that is at least divalent, comprising not less than two of at least one hydrophilic unit selected from hydrophilic units represented by structural formulae (3-3) to (3-6) above, and a branch unit selected from groups represented by structural formulae (3-7) to (3-9) below.

(3-7)

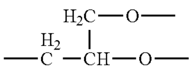

(3-8)

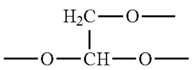

(3-9)

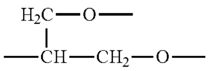

[8] The co-modified organopolysiloxane described in any one of [1] to [7], wherein in the general formulae (1) to (1-1-1), Q is a hydrophilic segment expressed by general formulae (4-1) to (4-7) below.

General Formula (4-1):

$$-R^3(-O-X^1_m-R^4)_p \quad (4\text{-}1)$$

wherein, $R^3$ is an organic group having (p+1) valency, and p is a number that is greater than or equal to 1 and less than or equal to 3; $X^1$ are each independently at least one hydrophilic unit selected from the hydrophilic units expressed by the general formulae (3-3) to (3-6) above, and m is a number in a range of 1 to 100; and $R^4$ is a hydrogen atom or a group selected from the group consisting of glycidyl groups, acyl groups, and alkyl groups having from 1 to 20 carbons;

General Formula (4-2):

$$—R^3(—O—X^2)_p \quad (4\text{-}2)$$

wherein, $R^3$ is a group synonymous with the group described above, p is a number synonymous with the number described above; and $X^2$ is a hydrophilic group represented by structural formula (4-2-1) below:

(4-2-1)

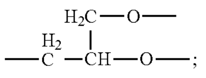

In this formula, the at least one hydrophilic unit selected from the hydrophilic units expressed by the general formulae (3-3) to (3-6) is bonded to two oxygen atoms, each independently;

General Formula (4-3):

$$—R^3(—O—X^3)_p \quad (4\text{-}3)$$

wherein $R^3$ is a group synonymous with the group described above, p is a number synonymous with the number described above; and $X^3$ is a hydrophilic group represented by structural formula (4-3-1) below.

(4-3-1)

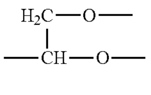

In this formula, the at least one hydrophilic unit selected from the hydrophilic units expressed by the general formulae (3-3) to (3-6) is bonded to two oxygen atoms, each independently;

General Formula (4-4):

$$—R^3(—O—X^4)_p \quad (4\text{-}4)$$

wherein $R^3$ is a group synonymous with the group described above, p is a number synonymous with the number described above; and $X^4$ is a hydrophilic group represented by structural formula (4-4-1) below.

(4-4-1)

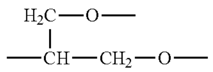

In this formula, the at least one hydrophilic unit selected from the hydrophilic units expressed by the general formulae (3-3) to (3-6) is bonded to two oxygen atoms, each independently.

[9] The co-modified organopolysiloxane described in any one of [1] to [8], that is represented by structural formula (1-1-A) or (1-1-B) below.

(1-1-A)

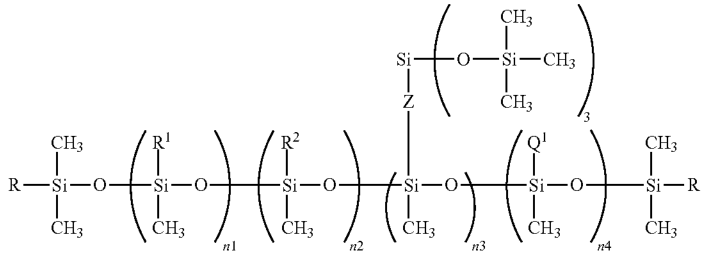

(1-1-B)

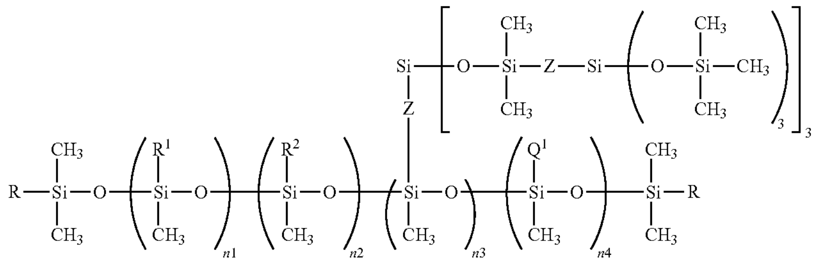

In these formulae, Z, $R^1$, and $R^2$ are groups synonymous with the groups described above; R is a group selected from the $R^1$, $R^2$, and $L^1$ moieties, and Q1, described hereinafter; (n1+n2+n3+n4) is a number in a range from 0 to 80; n1 is a number in a range from 0 to 70, n2 is a number in a range from 0 to 30, n3 is a number in a range from 1 to 20, and n4 is a number in a range from 0.1 to 2;

$Q^1$ are each independently a hydrophilic group selected from the group consisting of structural formulae (3'-1), (3'-2), (4-1-2), (4-2-2), (4-3-2), and (4-4-2) below.

(3'-1)

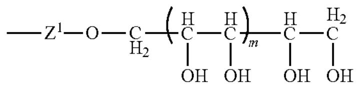

-continued (3'-2)

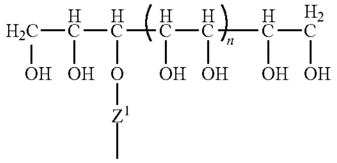

In these formulae, $Z^1$ is a substituted or unsubstituted straight or branched alkylene group having from 3 to 5 carbons, and m is 1 or 2;

(4-1-2)

$$-R^3-(O-X^1{}_m-R^4)_p$$

(4-2-2)

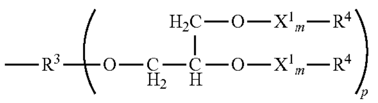

(4-3-2)

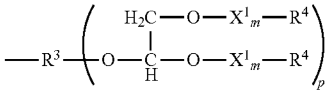

(4-4-2)

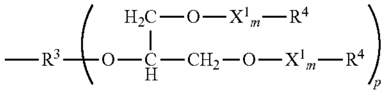

In these formulae, $R^3$ is an organic group having (p+1) valency, and p is a number that is greater than or equal to 1 and less than or equal 3; X1 are each independently at least one hydrophilic unit selected from the hydrophilic units expressed by the general formulae (3-3) to (3-6) above, and m is a number in a range of 1 to 100; and R4 is a hydrogen atom or a group selected from the group consisting of glycidyl groups, acyl groups, and alkyl groups having from 1 to 20 carbons.

[10] A surfactant or a surface treatment agent comprising the co-modified organopolysiloxane described in any one of [1] to [9].

[11] A powder treatment agent comprising the co-modified organopolysiloxane described in any one of [1] to [9].

[12] A powder composition comprising:

(A) the co-modified organopolysiloxane described in any one of [1] to [9]; and (B) a powder or coloring agent.

[13] The powder composition described in [12], wherein the component (B) is one or two or more selected from the group consisting of an inorganic pigment powder, an organic pigment powder, and a resin powder, having an average diameter in a range of 1 nm to 20 μm.

[14] A powder in oil dispersion comprising:

(A) the co-modified organopolysiloxane described in any one of [1] to [9], (B) a powder or coloring agent, and (C) one or more oil agent selected from a silicone oil, a nonpolar organic compound, and a low polarity organic compound that is liquid from 5° C. to 100° C.

[15] A preparation for external use comprising the co-modified organopolysiloxane described in any one of [1] to [10].

[16] The preparation for external use described in [15] that is a cosmetic composition or a medicament.

[17] A cosmetic composition comprising the powder composition described in claim [12] or [13].

[18] A cosmetic composition comprising the powder in oil dispersion described in [14].

[19] A make-up cosmetic composition comprising:

(A) the co-modified organopolysiloxane described in any one of [1] to [9];

(B) a powder or coloring agent; and (C) a silicone oil, a nonpolar organic compound, or a low polarity organic compound that is liquid from 5° C. to 100° C.

Advantageous Effects of Invention

With the present invention, a novel co-modified organopolysiloxane that can be advantageously used as a cosmetic composition raw material can be provided. Because this novel co-modified organopolysiloxane has a low viscosity and, preferably, a low HLD and a low degree of polymerization compared with conventional co-modified silicones, handling workability and fabrication efficiency of a powder dispersion and dispersibility of a powder in a mixed oil agent system is superior, and compatibility with a wide range of cosmetic raw materials is superior. As a result, preparation of particularly a powder in oil dispersion is facilitated and, moreover, a product characterized by having superior powder dispersibility and stability can be provided. Additionally, according to the present invention, a powder treatment agent comprising the organopolysiloxane, a powder that is surface treated using the powder treatment agent, a powder composition comprising the co-modified organopolysiloxane copolymer, and a powder in oil dispersion comprising an oil agent; and, moreover an external use preparation, particularly a make-up cosmetic composition can be provided. A variety of cosmetic compositions comprising the novel co-modified organopolysiloxane of the present invention can be provided. However, of these, a cosmetic composition using the powder in oil dispersion described above, particularly a make-up cosmetic composition can be advantageously provided.

DESCRIPTION OF EMBODIMENTS

Hereinafter, a novel co-modified organopolysiloxane of the present invention, uses thereof as various types of treatment agents (a surfactant or a surface treatment agent), particularly uses as a powder treatment agent and as a cosmetic raw material are described in detail. Additionally, detailed descriptions of a powder in oil dispersion, an external use preparation, advantageously a cosmetic composition, and particularly advantageously a make-up cosmetic composition using the novel co-modified organopolysiloxane of the present invention will be given.

It is possible to apply the novel co-modified organopolysiloxane according to the present invention to uses held in common with the co-modified organopolysiloxane recited in Patent Document 5 (WO2011/049248). That is, particularly in terms of the dosage form, type, and formulation examples of the cosmetic composition, the novel co-modified organopolysiloxane according to the present invention can be used as various treatment agents (a surfactant or a surface treatment agent), particularly as a powder treatment agent and a cosmetic raw material; can be used in combination with an optional cosmetic raw material component; and can be used as a external use preparation, in the same manner as the co-modified organopolysiloxane recited in Patent Document 5.

The co-modified organopolysiloxane according to the present invention is a co-modified organopolysiloxane having a group that has a siloxane dendron structure and a hydrophilic group, and a viscosity at 25° C. (hereinafter, unless otherwise dictated, referred to simply as "viscosity") that is not more than 1,500 mPa·s, and more specifically is a co-modified organopolysiloxane expressed by the following general formula (1). (Hereinafter, the group represented by $L^1$ in general formula (1), which is a silylalkyl group expressed by the following general formula (2) when i=1, is also referred to as the "carbosiloxane dendrimer" and the "silylalkyl group having a siloxane dendron structure".)

General Formula (1):

$$R^1_a R^2_b L^1_c Q_d SiO_{(4-a-b-c-d)/2} \quad (1)$$

In general formula (1), $R^1$ is a substituted or unsubstituted monovalent hydrocarbon group having from 1 to 30 carbons, or a hydrogen atom; $R^2$ is a substituted or unsubstituted straight or branched monovalent hydrocarbon group having from 6 to 30 carbons; $L^1$ is a silylalkyl group having a siloxane dendron structure expressed by the following general formula (2) when i=1; and Q is a hydrophilic segment.

General Formula (2)

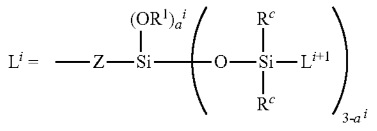

(2)

In general formula (2), $R^1$ is a group synonymous with the group described above, $R^C$ is an alkyl group having 1 to 6 carbons or a phenyl group, and Z is a divalent organic group; i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c; and $a^i$ is a number in a range of 0 to 3. Additionally, a, b, and c are in ranges so that $1.0 \le a+b \le 2.5$, $0.001 \le b \le 0.5$, and $0.001 \le c \le 1.5$.

The viscosity of the co-modified organopolysiloxane according to the present invention is not more than 1,500 mPa·s, and is preferably in a range from 50 to 1,400 mPa·s, more preferably in a range from 150 to 1,350 mPa·s, and even more preferably in a range from 200 to 1,300 mPa·s. If the viscosity of the co-modified organopolysiloxane exceeds the upper limit described above, handling workability when used as a powder treatment agent will be negatively affected. Particularly, efficiency when fabricating a dispersion will easily decline and, particularly, performance will be insufficient from the perspective of dispersibility of the powder. More specifically, if the viscosity of the co-modified organopolysiloxane exceeds the upper limit described above, the viscosity of an obtained powder dispersion (particularly a slurry powder in oil dispersion) will increase with time and/or dispersion of the powder will be insufficient, thus leading to difficulty when using the co-modified organopolysiloxane as a cosmetic raw material. Moreover, depending on the preparation conditions, in some cases, it may be impossible to fabricate a powder dispersion.

In general formula (1), $R^1$ is a substituted or unsubstituted monovalent hydrocarbon group having from 1 to 30 carbons, or a hydrogen atom. However, the monovalent organic group $R^1$ does not comprise a group corresponding with the $L^1$ or Q moieties described above and, particularly independently represents an aryl group or an alkyl group having from 1 to 10 carbons. Examples thereof include methyl, ethyl, n-propyl, i-propyl, n-butyl, i-butyl, s-butyl, pentyl, neopentyl, cyclopentyl, hexyl, and similar straight, branched, or annular alkyl groups; and a phenyl groups. From a technical point of view, $R^1$ preferably is a methyl group or a phenyl group. Additionally, $R^1$ may be a group wherein the hydrogen atoms bonded to the carbon atoms of these groups are substituted at least partially by fluorine or a similar halogen atom, or by an organic group having an epoxy group, an acyl group, a carboxyl group, an amino group, a (meth)acryl group, a mercapto group, or the like.

$R^2$ is a functional group that is comprised optionally in the co-modified organopolysiloxane according to the present invention and is a substituted or unsubstituted, straight or branched monovalent hydrocarbon group having from 6 to 30 carbons. Particularly, in cases where all of the $R^1$ moieties are alkyl groups having not more than 5 carbons (particularly methyl groups) or are phenyl groups, it is preferable that the long chain hydrocarbon group $R^2$ be comprised for the purpose of improving affinity with, particularly, hydrocarbon-based oil agents (i.e. cosmetic raw materials). Preferable examples of the $R^2$ moiety include hexyl groups, heptyl groups, octyl groups, decyl groups, dodecyl groups, and similar alkyl groups having not less than 6 carbons; cyclohexyl groups and similar cycloalkyl groups; tolyl groups, xylyl groups, naphthyl groups, and similar aryl groups; and groups wherein the hydrogen atoms bonded to the carbon atoms of these groups are substituted at least partially by fluorine or a similar halogen atom, or an organic group having an epoxy group, an acyl group, a carboxyl group, an amino group, a (meth)acryl group, a mercapto group, or the like. The $R^2$ moiety is preferably an alkyl group having from 8 to 20 carbons.

In general formula (1), the group represented by $L^1$ is a silylalkyl group having a carbosiloxane dendrimer structure, and is defined as the silylalkyl group expressed by general formula (2) when i=1. The silylalkyl group having a carbosiloxane dendrimer structure has a structure where a carbosiloxane unit is extended in the form of a dendrimer and, thus, compared to a linear or simply branched polysiloxane unit, is a functional group that exhibits high water repellency; and, thus, a superior surfactant or powder treatment agent can be provided to the organopolysiloxane copolymer according to the present application without inhibiting the tactile sensation originating from the hydrophilic functional group. Additionally, the silylalkyl group having a carbosiloxane dendrimer structure is chemically stable, and for this reason, the silylalkyl group is a functional group providing advantageous properties such as usability in combination with a wide range of cosmetic composition-use components.

In general formula (2), $R^C$ is a phenyl group or an alkyl group having from 1 to 6 carbons. Examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups. From an industrial perspective, $R^C$ is preferably a methyl group or a phenyl group.

In general formula (2), i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and, is a methyl group or a phenyl group when i=c. In particular, $L^i$ is preferably a methyl group when i=c.

From a technical standpoint, the number of generations c is preferably an integer from 1 to 3, and more preferably is 1 or 2. In each of the number of generations, the group represented by $L^1$ is expressed as follows. In these formulae, $R^2$ and Z are groups synonymous with the groups described above.

When the number of generations c=1, $L^1$ is expressed by the following general formula (2-1).

General Formula (2-1)

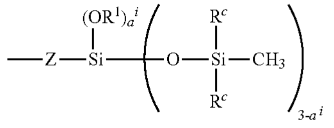

When the number of generations c=2, $L^1$ is expressed by the following general formula (2-2).

General Formula (2-2)

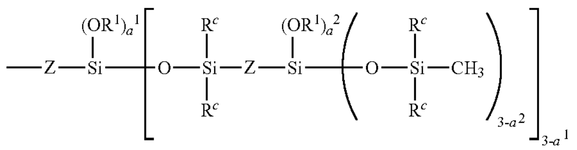

When the number of generations c=3, $L^1$ is expressed by the following general formula (2-3).

following general formulae (5-1) to (5-7). Of these, the Z in $L^1$ is preferably a divalent organic group expressed by general formula (5-1) that is introduced by a reaction between a silicon-bonded hydrogen atom and an alkenyl group. Likewise, Z is preferably a divalent organic group expressed by general formula (5-3) that is introduced by a reaction between a silicon-bonded hydrogen atom and an unsaturated carboxylic functional group. On the other hand, in the silylalkyl group represented by $L^i$ in which the number of generations c is 2 or more, and $L^1$ is $L^2$ to $L^C$, Z is preferably an alkylene group having from 2 to 10 carbons, more preferably a group selected from an ethylene group, a propylene group, a methylethylene group, and a hexylene group, and most preferably an ethylene group.

$$—R^6—$$ (5-1)

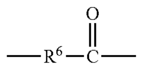
(5-2)

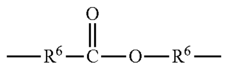
(5-3)

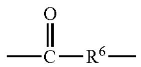
(5-4)

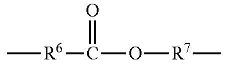
(5-5)

General Formula (2-3)

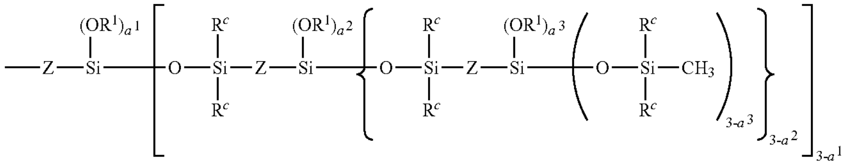
(2-3)

In formula (2), $a^i$ are each independently a number in a range from 0 to 3 and, in a structure represented by formulae (2-1) to (2-3) where the number of generations is from 1 to 3, $a^1$, $a^2$, and $a^3$ are each independently a number in a range from 0 to 3. The $a^i$ moieties are preferably a number in a range from 0 to 1 and more preferably the $a^i$ moieties are 0.

In general formulae (2) and (2-1) to (2-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a carbosiloxane dendrimer structure, the functional group can be appropriately selected and is not restricted to the functional groups described above.

More specifically, Z are each independently a group selected from divalent organic groups expressed by the -continued

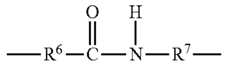
(5-6)

$$—R^6—R^7—$$ (5-7)

In these formulae (5-1) to (5-4), $R^6$ may have a substituent, and are each independently a straight or branched chain alkylene group or alkenylene group having from 2 to 22 carbons, or an arylene group having from 6 to 22 carbons. More specifically, examples of $R^6$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^6$ is preferably a group selected from an ethylene group, a propylene group, a methylethylene group, and a hexylene group.

In formulae (5-5) to (5-7), $R^7$ is a group selected from divalent organic groups expressed by the following formulae.

$-(CH_2)_2-O-(CH_2)_3-$,

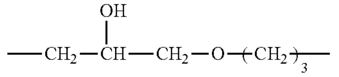

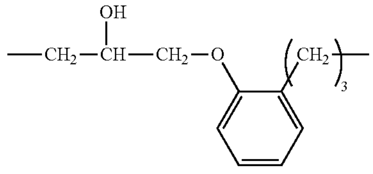

,

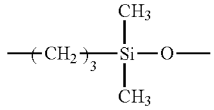

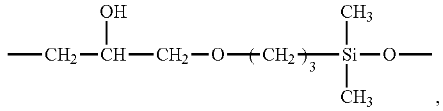

,

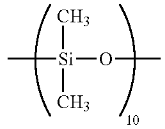

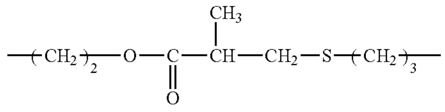

Q is a hydrophilic group comprising a sugar alcohol represented by structural formulae (3-1) and (3-2) below, or a hydrophilic group comprising at least one hydrophilic unit selected from hydrophilic units represented by structural formulae (3-3) to (3-6) below. The hydrophilic group Q is a moiety that imparts hydrophilicity to the co-modified organopolysiloxane according to the present application and, generally, is a functional group derived from a hydrophilic compound. Preferable examples of Q as defined above include at least monovalent alcohols, polyether-based compounds, (poly)glycerin-based compounds, (poly)glycidyl ether-based compounds, and functional groups derived from hydrophilic sugars, that may be partially capped at the molecular end by a hydrocarbon. From the perspective of properties as a powder treatment agent, particularly dispersibility properties of an inorganic powder, with the co-modified organopolysiloxane according to the present invention, in Formula (1) and the like described above, Q is preferably a polyhydric alcohol-containing organic group, and more preferably is a (poly)glycerin residue. Particularly, Q is a hydrophilic group derived from a (poly)glycerin-based compound, and most preferably is a hydrophilic group derived from (poly)glycerin. Specifically, Q preferably is a (poly)glycerin monoallyl ether or a (poly)glyceryl eugenol, which are examples of hydrophilic groups derived from a (poly)glycerin-based compound having a monoglycerin, a diglycerin, a triglycerin, or a tetraglycerin structure.

More specifically, Q is a sugar alcohol-containing organic group represented by structural formula (3-1) below.

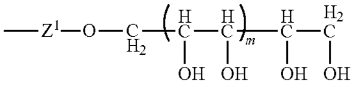

(3-1)

In this formula, $Z^1$ is a substituted or unsubstituted straight or branched alkylene group having from 3 to 5 carbons, and m is 1 or 2; or a sugar alcohol-containing organic group represented by structural formula (3-2) below.

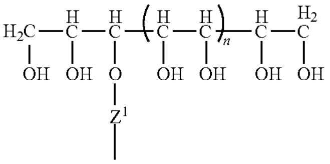

(3-2)

In this formula, $Z^1$ is synonymous with that described above, and n is 0 or 1; or a hydrophilic group bonded to the silicon atom via a linking group that is at least divalent, comprising not less than one type of hydrophilic unit selected from the hydrophilic units represented by structural formulae (3-3) to (3-6) below.

$$-C_rH_{2r}-O- \quad (3\text{-}3)$$

The hydrophilic unit represented by formula (3-3) is an oxyalkylene unit. In this formula, r is a number in a range from 1 to 6, and is preferably a number in a range from 2 to 4. The hydrophilic unit represented by formula (3-3) can have 1 or more hydrophilic groups (Q). Additionally, the hydrophilic unit represented by (3-3) is preferably included in the hydrophilic group (Q) as a polyoxyalkylene unit where from 2 to 50 of the hydrophilic units expressed by formula (3-3) are linked and r are each independently from 2 to 4.

Particularly, from the perspective of hydrophilicity, the hydrophilic unit expressed by formula (3-3) preferably is included in the hydrophilic group Q as 4 to 50 linked polyoxyalkylene units, and more preferably as one or more type of the polyoxyalkylene unit expressed by formula (3-3-1).

$$-(C_2H_4O)_{t1}(C_3H_6O)_{t2}- \quad (3\text{-}3\text{-}1)$$

In this formula, t1 and t2 are each numbers greater than or equal to 0, and (t1+t2) is a number in a range from 4 to 50 and preferably in a range from 8 to 30.

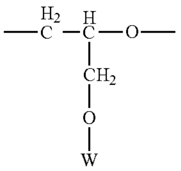

(3-4)

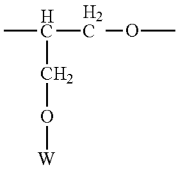

(3-5)

-continued (3-6)

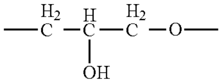

In formulae (3-4) to (3-6), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units represented by structural formulae (3-4) to (3-6) are hydrophilic units included in a hydrophilic group derived from a hydrophilic compound selected principally from polyhydric alcohols including glycerin, (poly) glycerines (also called "(poly)glycerols"), and (poly)glycidyl ethers or compounds in which terminal hydroxyl groups thereof are partially capped by hydrocarbon groups. However, the hydrophilic units are not limited thereto.

In general formula (1), Q may be, for example, a hydrophilic group that does not have a branched structure such as a straight polyoxyalkylene group, and may also be a hydrophilic group that has a partial branched structure in the functional group such as a (poly)glycerol group or a (poly) glycidyl ether group.

More specifically, Q may be a hydrophilic segment bonded to the silicon atom via a linking group that is at least divalent, comprising at least one linearly bonded hydrophilic unit selected from hydrophilic units represented by the following structural formulae (3-3) to (3-6); or, furthermore, Q may be a hydrophilic segment bonded to the silicon atom via a linking group that is at least divalent, comprising not less than one of at least one hydrophilic unit selected from hydrophilic units represented by structural formulae (3-3) to (3-6) above, and a branch unit selected from groups represented by structural formulae (3-7) to (3-9) below.

(3-7)

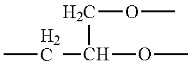

(3-8)

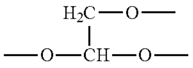

(3-9)

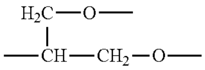

The linking group that is at least divalent is a bonding site with respect to the silicon atom included in the hydrophilic group (Q), and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

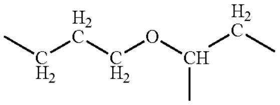

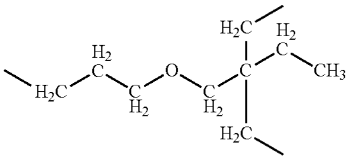

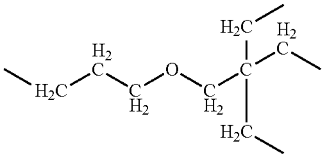

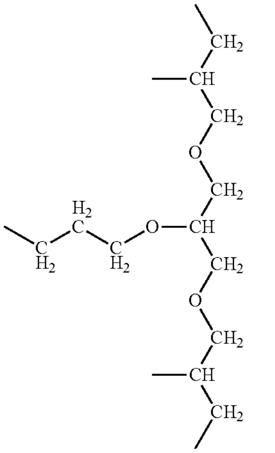

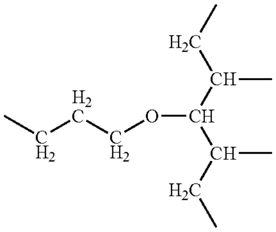

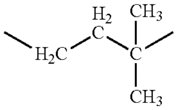

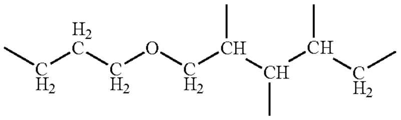

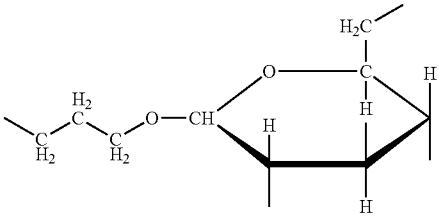

Q is more preferably a hydrophilic group expressed by the following general formulae (4-1) to (4-3).

General Formula (4-1):

$$—R^3(—O—X^1_m—R^4)_p \quad (4-1)$$

In this formula, $R^3$ is an organic group having (p+1) valency, and p is a number that is greater than or equal to 1 and less than or equal to 3. Examples of $R^3$ include a group that is synonymous with the linking group that is at least divalent.

It is particularly preferable that p is 1 and that $R^3$ is a group selected from the divalent organic groups expressed by the following general formula.

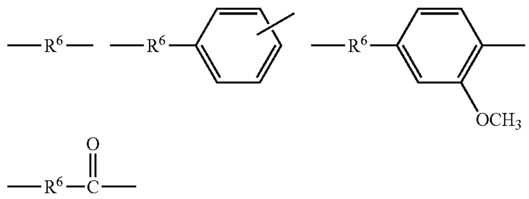

In this formula, $R^6$ may have a substituent, and are each independently a straight or branched chain alkylene group or alkenylene group having from 2 to 22 carbons, or an arylene group having from 6 to 22 carbons.

$X^1$ are each independently at least one hydrophilic unit selected from the hydrophilic units expressed by the general formulae (3-3) to (3-6) above, and m is a number in a range of 1 to 100. In this case, when $X^1$ is the hydrophilic unit (alkyleneoxy group) expressed by the general formula (3-3), m is preferably a number in a range from 4 to 50, and a structure represented by $[-X^1_m-]$ is more preferably a polyoxyalkylene unit expressed by the formula (3-3-1). Additionally, when $X^1$ comprises the hydrophilic unit expressed by the general formulae (3-4) to (3-6), m is preferably a number in a range from 1 to 50, and more preferably is a number in a range from 1 to 15. $R^4$ is a hydrogen atom or a group selected from the group consisting of glycidyl groups, acyl groups, and alkyl groups having from 1 to 20 carbons, and preferably is a hydrogen atom or a methyl group.

General Formula (4-2):

$$-R^3(-O-X^2)_p \quad (4\text{-}2)$$

In this formula, $R^3$ is a group synonymous with the group described above, and p is a number synonymous with the number described above. $X^2$ is a hydrophilic group represented by structural formula (4-2-1) below.

(4-2-1)

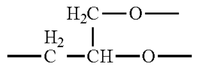

In this formula, the at least one hydrophilic unit selected from hydrophilic units expressed by the general formulae (3-3) to (3-6) is bonded to two oxygen atoms, each independently. The hydrophilic unit may further be bonded to a branch unit selected from groups represented by structural formulae (3-7) to (3-9). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic group expressed by general formula (4-2) include hydrophilic groups expressed by the following general formula (4-2-2). In this formula, p, $R^3$, $X^1$, $R^4$, and m are synonymous with those described above (4-2-2)

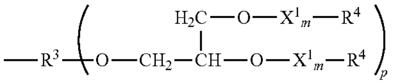

General Formula (4-3):

$$-R^3(-O-X^3)_p \quad (4\text{-}3)$$

In this formula, $R^3$ is a group synonymous with the group described above, and p is a number synonymous with the number described above. $X^3$ is a hydrophilic group represented by structural formula (4-3-1) below:

(4-3-1)

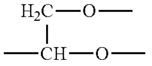

In this formula, the at least one hydrophilic unit selected from hydrophilic units expressed by the general formulae (3-3) to (3-6) is bonded to two oxygen atoms, each independently. The hydrophilic unit may further be bonded to a branch unit selected from groups represented by structural formulae (3-7) to (3-9). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic group expressed by general formula (4-3) include hydrophilic groups expressed by the following general formula (4-3-2). In this formula, p, $R^3$, $X^1$, $R^4$, and m are synonymous with those described above.

(4-3-2)

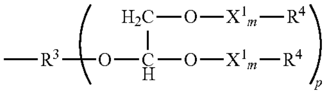

General Formula (4-4):

$$-R^3(-O-X^4)_p \quad (4\text{-}4)$$

In this formula, $R^3$ is a group synonymous with the group described above, and p is a number synonymous with the number described above. $X^4$ is a hydrophilic group represented by structural formula (4-4-1) below:

(4-4-1)

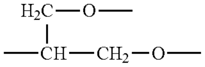

In this formula, the at least one hydrophilic unit selected from hydrophilic units expressed by the general formulae (3-3) to (3-6) is bonded to two oxygen atoms, each independently. The hydrophilic unit may further be bonded to a branch unit selected from groups represented by structural formulae (3-7) to (3-9). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic group expressed by general formula (4-4) include hydrophilic groups expressed by the following general formula (4-4-2).

In this formula, p, $R^3$, $X^1$, $R^4$, and m are synonymous with those described above.

(4-4-2)

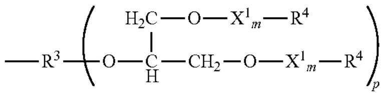

In general formula (1), a, b, c, and d are numbers in ranges so that $1.0 \leq a+b \leq 2.5$, $0.001 \leq c \leq 1.5$, and $0.001 \leq d \leq 1.5$. That is, provided that the co-modified organopolysiloxane of the present invention has the group having the siloxane dendron structure and the hydrophilic group and has a low viscosity of not higher than 1,500 mPa·s, the co-modified organopolysiloxane may take any straight, branched chain, cyclic, or network siloxane bonded form, but from the perspective of use as a powder treatment agent, preferably is a straight or branched chain co-modified organopolysiloxane.

Additionally, the co-modified organopolysiloxane of the present invention preferably has a hydrophile-liophile balance value (HLB value) that is not greater than 2.0 and more preferably in a range from 0.1 to 2.0. Note that the HLB value is imparted by formula (A) below. In general formula (1), the values of a to d, and particularly the value of c, are preferably numbers such that the HLB value of the entire molecule will be not greater than 2.0.

HLB=(total molecular weight of hydrophilic group moiety/total molecular weight)×20 (A)

The HLB value being equal to or less than the upper limit described above (low HLB) means that the co-modified organopolysiloxane of the present invention advantageously has a low content of the hydrophilic group (Q). If the content of the hydrophilic groups is high, the polyglycerol and the sugar alcohol residue will have many hydroxyl groups and the viscosity of the co-modified organopolysiloxane itself will tend to increase due to cohesive force resulting from hydrogen bonding. As a result, handling workability may be negatively affected in cases when used as a powder treatment agent.

Preferable examples of the co-modified organopolysiloxane according to the present application include a straight co-modified organopolysiloxane represented by structural formula (1-1) below.

(1-1)

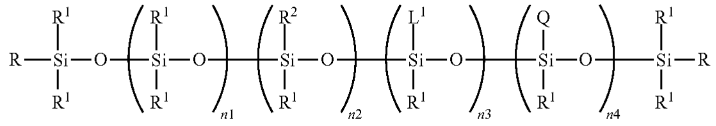

In this formula, $R^1$, $R^2$, $L^1$ and Q are groups synonymous with the groups described above, and R is a group selected from $R^1$, $R^2$, $L^1$, and Q. However, when n3=0, at least one R is $L^1$, and when n4=0, at least one R is Q.

The straight co-modified organopolysiloxane represented by structural formula (1-1) preferably has a viscosity of not more than 1,500 mPa·s and a HLB value of not more than 2.0. Specifically, each of n1 to n4 which represent the average degree of polymerization of each of the diorganosiloxy units is in a range such that (n1+n2+n3+n4) is from 2 to 80, preferably from 10 to 75, and more preferably from 15 to 70.

n1 is a number in a range from 0 to 70, preferably from 5 to 70, and more preferably from 10 to 70.

n2 is a number in a range from 0 to 30, preferably from 0 to 20, and more preferably from 0 to 15.

n3 is a number in a range from 1 to 20, preferably from 1 to 15, and more preferably from 1 to 10.

n4 is a number in a range from 1 to 2, preferably from 0.2 to 1.8, and more preferably from 0.3 to 1.5. Additionally, n4 affects the content of the hydrophilic group Q and, therefore, n4 is particularly preferably a number in a range such that the HLB value of the entire molecule is not more than 2.0.

Industrially preferable examples of the co-modified organopolysiloxane according to the present application include a straight co-modified organomethylpolysiloxane represented by structural formula (1-1-1) below.

(1-1-1)

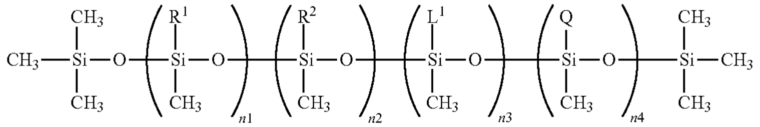

In this formula, $R^1$, $R^2$, $L^1$, and Q are groups synonymous with the groups described above, and n1 to n4 are numbers synonymous with the numbers described above.

Particularly preferable examples of the co-modified organopolysiloxane according to the present application include co-modified organopolysiloxanes represented by the following structural formulae (1-1-A) and (1-1-B).

(1-1-A)

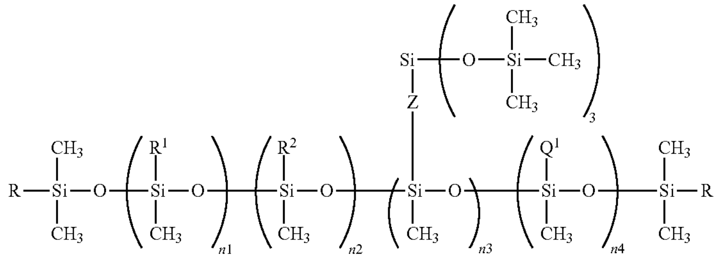

(1-1-B)

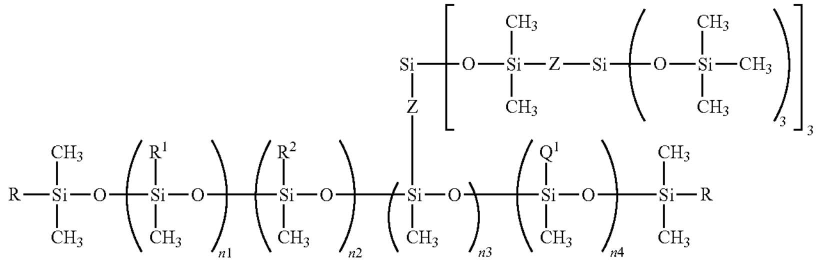

In the structural formula (1-1-1) or (1-1-2), Z, $R^1$, and $R^2$ are groups synonymous with the groups described above, and n1 to n4 are numbers synonymous with the numbers described above. $Q^1$ are each independently a hydrophilic group selected from the group consisting of structural formulae (3'-1), (3'-2), (4-1-2), (4-2-2), (4-3-2), and (4-4-2) below. In these formulae $Z^1$, $R^3$, $X^1$, and $R^4$ are groups synonymous with the groups described above, and p and m are numbers synonymous with the numbers described above.

(3'-1)

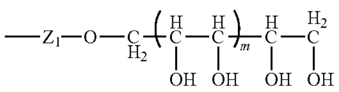

(3'-2)

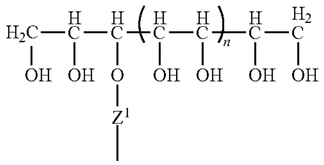

(4-1-2)

$$-R^3-(O-X^1{}_m-R^4)_p$$

(4-2-2)

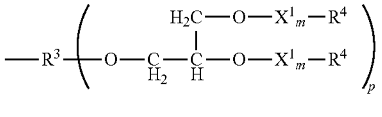

(4-3-2)

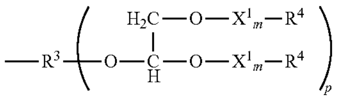

(4-4-2)

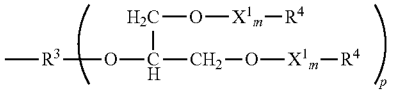

In the structural formula (1-1) above, Q are each independently a sugar alcohol-containing organic group represented by structural formula (3'-1) or (3'-2). In the sugar alcohol-modified organopolysiloxane according to the present invention, all of the Q moieties may be the sugar alcohol-containing organic group represented by the general formula (3'-1) or the general formula (3'-2), or a portion of the Q moieties in one molecule may be the sugar alcohol-containing organic group represented by the general formula (3'-1) and the remainder of the Q moieties may be the sugar alcohol-containing organic group represented by the general formula (3'-2).

Furthermore, the sugar alcohol-modified organopolysiloxane according to the present invention may be one type or a mixture of two or more types of sugar alcohol-modified organopolysiloxanes expressed by the formulae (1), (1-1), (1-1-1), (1-1-A), and (1-1-B) above.

Particularly, from t the perspective of properties as a powder treatment agent, particularly dispersibility properties of an inorganic powder, with the sugar alcohol-modified organopolysiloxane according to the present invention, in the formula (1) and the like, the Q moieties are preferably a xylitol residue (sugar alcohol-containing organic group).

As described above, the xylitol residue is a group represented by structural formula: $-C_3H_6-OCH_2[CH(OH)]_3CH_2OH$, or structural formula: $-C_3H_6-OCH\{CH(OH)CH_2OH\}_2$, and in the sugar alcohol-modified organopolysiloxane according to the present invention, the xylitol residue may comprise one type or two types of these xylitol residues. Thus, in the general formula (1-1), all of the Q moieties may comprise only the xylitol residue represented by the structural formula: $-C_3H_6-OCH_2[CH(OH)]_3CH_2OH$ or the structural formula: $-C_3H_6-OCH\{CH(OH)CH_2OH\}_2$ or, alternatively, X' may by constituted by the two types of xylitol residues represented by the structural formula: $-C_3H_6-OCH_2[CH(OH)]_3CH_2OH$ and the structural formula: $-C_3H_6-OCH\{CH(OH)CH_2OH\}_2$. In the latter case, a composition ratio (matter weight ratio) thereof is preferably in a range from 5:5 to 10:0 and is more preferably in a range from 8:2 to 10:0. Note that when the composition ratio is 10:0, the Q moieties are constituted substantially only by the xylitol residue represented by the structural formula: $—C_3H_6—OCH_2[CH(OH)]_3CH_2OH$.

Additionally, in cases where the sugar alcohol-modified organopolysiloxane according to the present invention is a mixture of two or more types of sugar alcohol-modified organopolysiloxanes, the mixture can comprise at least two types of sugar alcohol-modified organopolysiloxanes selected from the group consisting of: a sugar alcohol-modified organopolysiloxane in which all of the Q moieties in general formula (1-1) are the xylitol residue represented by the structural formula: $—C_3H_6—OCH_2[CH(OH)]_3CH_2OH$; a sugar alcohol-modified organopolysiloxane in which all of the Q moieties in the general formula (1-1) are the xylitol residue represented by the structural formula: $—C_3H_6—OCH\{CH(OH)CH_2OH\}_2$; and a sugar alcohol-modified organopolysiloxane in which the Q moieties in the general formula (1-1) consist of two types of xylitol residues represented by the structural formula: $—C_3H_6—OCH_2[CH(OH)]_3CH_2OH$ and the structural formula: $—C_3H_6—OCH\{CH(OH)CH_2OH\}_2$ (where a composition ratio (matter weight ratio) is preferably in a range from 5:5 to 10:0 and more preferably in a range from 8:2 to 10:0). Furthermore, with the sugar alcohol-modified organopolysiloxane according to the present invention, the Q moieties in the general formula (1-1) may be constituted by the two types of xylitol residues represented by the structural formula: $—C_3H_6—OCH_2[CH(OH)]_3CH_2OH$ and the structural formula: $—C_3H_6—OCH\{CH(OH)CH_2OH\}_2$ (where a composition ratio (matter weight ratio) is particularly preferably in a range from 5:5 to 10:0 and more preferably in a range from 8:2 to 10:0); and may be a mixture of two or more types of sugar alcohol-modified organopolysiloxanes having different composition ratios.

Examples of the $R^4$ moiety include divalent hydrocarbon groups having from 3 to 5 carbons, and examples of the $R^5$ moiety include monovalent hydrocarbon groups having from 1 to 8 carbons, as described above.

The co-modified organopolysiloxane according to the present application described above can be obtained by addition-reacting a hydrophilic compound, which has an alkenyl group or similar reactive functional group and a compound with a siloxane dendron structure having one carbon-carbon double bond at one end of the molecular chain, with an organopolysiloxane that has a Si—H or similar reactive functional group. Note that the co-modified organopolysiloxane according to the present application described above can be obtained by further addition-reacting an unsaturated long chain hydrocarbon compound having a carbon-carbon double bond on one end of the molecular chain. The type of addition reaction is not particularly limited but, from the standpoint of reaction control, purity, and yield, the addition reaction is preferably performed in the presence of a hydrosilylation reaction catalyst. Additionally, a crude co-modified organopolysiloxane product obtained via the addition reaction may be refined by performing a deodorizing treatment by hydrogenation reaction in the presence of a hydrogenation catalyst in a solvent or without a solvent; or may be subjected to an odor attenuating treatment using an acidic substance. Furthermore, the co-modified organopolysiloxane may be a mixture with a hydrophilic compound having an alkenyl group or similar reactive functional group.

With regards to the synthesis of the co-modified organopolysiloxane according to the present application, the same method recited in paragraphs 0110 to 0122 of Patent Document 5 (WO2011/049248, filed by the present applicant), specifically, reacting, refining, and odor attenuating treating or the like using an acidic substance, can be used. Note that in cases where the hydrophilic group Q is a sugar alcohol-modified group, it is possible to make the co-modified organopolysiloxane substantially odorless and, because of this, performing the odor attenuating treatment using an acidic substance as recited in Japanese Patent Application No. 2011-121094 (filed by the present applicant) is particularly preferable from the perspective of providing a substantially odorless cosmetic raw material.

Uses of the Co-Modified Organopolysiloxane

The novel co-modified organopolysiloxane according to the present invention (hereinafter, referred to as "component (A)") is hydrophobic, has a silylalkyl group having a siloxane dendron structure that provides high water repellency and a hydrophilic group in the same molecule, and has low viscosity and generally low HLB. Therefore, handling, working efficiency, and compounding stability with oleophilic raw materials are superior. As a result, the novel co-modified organopolysiloxane according to the present invention is useful as various types of treatment agents and cosmetic raw material components, particularly as a surfactant or a surface treatment agent for use in a cosmetic composition, and more particularly is extremely useful as a powder treatment agent or powder dispersing agent for use in surface treating a powder or dispersing a powder.

Uses as a surfactant of the novel co-modified organopolysiloxane according to the present invention and preparations of emulsion compositions are the same as those recited for the co-modified organopolysiloxane in paragraphs 0124 to 0147 of Patent Document 5 (WO2011/049248, filed by the present applicant). When preparing each of the emulsion compositions, the novel co-modified organopolysiloxane according to the present invention (low viscosity and, preferably, low HLB) can be combined with the co-modified organopolysiloxane recited in Patent Document 5 and emulsified. Particularly, the co-modified organopolysiloxane according to the present invention is preferable as a surfactant for use in a water-in-oil emulsion cosmetic.

Other Uses

The novel co-modified organopolysiloxane according to the present invention can also be used as a tactile sensation improver, a moisturizing agent, a binder, and a skin adhesive. Additionally, the novel co-modified organopolysiloxane according to the present invention can be combined with water for use as a film agent or a viscosity adjusting agent.

Use as a Powder Treatment Agent

The co-modified organopolysiloxane according to the present invention has low viscosity and, preferably, low HLB and can be oriented on the surface of various powders so as to impart an appropriate degree of water repellency. Therefore, the co-modified organopolysiloxane according to the present invention can be used for surface treating and dispersing powders for use in cosmetic compositions, and can be advantageously used as a powder surface treating agent. Particularly, when used as a powder treatment agent, dispersion stability in a mixed oil agent system of the co-modified organopolysiloxane according to the present invention is superior compared to conventional co-modified organopolysiloxanes. Thus, a powder in oil dispersion having superior stability in which the powder does not agglomerate or precipitate after preparing a powder composition obtained by treating the powder surface using a treatment agent can be provided, even when a method is used where the powder composition is dispersed in an oil agent dispersing medium and even when the powder is one where conventional powder treatment agents result in difficulties in stable dispersion.

The co-modified organopolysiloxane of the present invention has excellent compatibility with various other hydrophilic and hydrophobic components in the cosmetic composition, and can enhance the dispersibility and stability of a powder in a cosmetic composition that comprises a powder. Thus, the powder treatment agent of the present invention and the powder surface treatment agent of the present invention can improve the stability of a cosmetic composition that comprises a powder and can improve the uniform dispersibility of said powder. A cosmetic composition that comprises a powder that is surface treated using the powder surface treatment agent has high stability and said powder uniformly disperses in said the cosmetic composition.

A compounded amount of the co-modified organopolysiloxane in the powder treatment agent of the present invention is not particularly limited provided that powder treatment effects are displayed and, for example, can be from 50 to 100 wt. % (mass %), and is preferably from 70 to 100 wt. %, and more preferably from 90 to 100 wt. %.

The powder treatment agent of the present invention may comprise a combination of the co-modified organopolysiloxane according to the present invention and another known surface treatment agent and be used to surface treat a powder. Examples of the other surface treatment agent include surface treatment agents based on methylhydrogenpolysiloxane, silicone resin, metal soap, silane coupling agents, silica, alumina, titanium oxide, and similar inorganic oxides; perfluoroalkylsilane, perfluoroalkyl phosphate ester salts, and similar fluorine compounds. Thus, the powder surface treatment agent of the present invention may, for example, comprise from 0.1 to 50 wt. % of the other surface treatment agent and preferably comprises from 1 to 30 wt. % and more preferably comprises from 5 to 10 wt. % of the other surface treatment agent.

When using the co-modified organopolysiloxane according to the present invention as the powder surface treatment agent, a compounded amount of the co-modified organopolysiloxane and the powder or coloring agent is preferably in a range from 0.1 to 30 parts by mass, and more preferably from 0.5 to 10 parts by mass per 100 parts by mass of the powder or coloring agent. If the compounded amount is less than the lower limit described above, effects by the surface treating may be insufficient. On the other hand, even if the compounded amount exceeds the upper limit described above, greater prominent changes in texture will not occur, and the tendency for the powder and the co-modified organopolysiloxane to form a uniform mixture will increase.

The co-modified organopolysiloxane according to the present invention can be used to treat a powder surface using a conventional method. This method is not particularly limited and, for example, can be appropriately selected from the methods described below.

1. A method in which the target powder is surface treated by being dispersed in a medium selected from organic solvents in which the treatment agent has been compounded.
2. A method in which the powder is surface treated by mixing the powder and the powder treatment agent and, thereafter, crushing the mixture in a pulverizer such as a ball mill, a jet mill, or the like.
3. A treatment method in which the treatment agent is compounded in a solvent, the powder is dispersed in the mixture so as to adhere the treatment agent to the surface of the powder, and then the powder is dried and sintered.

Powder Composition

Additionally, the present invention relates to a powder composition comprising (A) the co-modified organopolysiloxane according to the present invention and (B) a powder or coloring agent. The powder composition can be obtained, according to the methods described above or the like, by mixing (B) the powder or coloring agent and (A) the co-modified organopolysiloxane according to the present invention, regardless of the purpose (i.e. to surface treat the powder, improve dispersibility of the powder, to act as a premix for a cosmetic raw material, or the like).

Powder in Oil Dispersion

Additionally, "powder in oil dispersion" as used in the present invention, refers to a product in which a powder composition obtained as described above is dispersed in an oil agent or, alternately, a product in which a co-modified organopolysiloxane is dissolved or dispersed in an oil agent, and then the powder is added by being mixed and dispersed therein; and a form thereof is that of a liquid dispersed product. This liquid dispersed product is also called a "slurry". Particularly, the co-modified organopolysiloxane according to the present invention is useful on the point that a low viscosity slurry can be prepared under the same conditions as the co-modified organopolysiloxane recited in Patent Document 5 above, even when the powder is a powder that cannot be sufficiently treated such as zinc oxide or a similar inorganic powder.

The oil agent is not particularly limited provided that a liquid dispersion can be prepared, and is an oil agent that is commonly used as a component of a cosmetic composition. Furthermore, while the oil agent is typically liquid at room temperature, it may by solid such as a wax, and may also be in a highly viscous (high viscosity) gum-like state or paste-like state. The oil agent is preferably one or more selected from (C) a silicone oil, a nonpolar organic compound, and a low polarity organic compound that are liquid from 5 to 100° C.

The powder in oil dispersion of the powder in oil dispersion can be appropriately prepared according to a known method such as the methods described below.

1. A method in which the powder composition obtained as described above is added to and dispersed in ester oil, silicone oil, or a similar oil agent.
2. A method in which the co-modified organopolysiloxane is dissolved or dispersed in the oil agent described above, the powder is added thereto, and the mixture is blended using a ball mill, a bead mill, a sand mill, or a similar disperser. The obtained powder in oil dispersion can be compounded as-is in a preparation for external use (particularly in a cosmetic composition).

The powder composition and the powder in oil dispersion comprising the co-modified organopolysiloxane according to the present invention can be suitably used as a preparation for external use, particularly for a cosmetic composition or a cosmetic raw material.

(B) Powder or Coloring Agent

The powder or coloring agent (B) used in the powder composition, the powder in oil dispersion, and the like according to the present invention is a component that is commonly used in a cosmetic composition and includes white and colored pigments as well as extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range from 1 nm to 100 μm. Particularly, when compounding the powder or coloring agent as a pigment, preferably one or two or more selected from an inorganic pigment powder, an organic pigment powder, and a resin powder having an average diameter in a range from 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants recited in paragraphs 0150 to 0152 of Patent Document 5 (WO2011/049248, filed by the present applicant).

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the sidechain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. When surface treatment is performed using the co-modified organopolysiloxane, a luxurious tactile sensation can be imparted without reducing the suede-like tactile sensation of the silicone elastomer powder. Furthermore, in cases where the silicone elastomer powder and the co-modified organopolysiloxane are compounded in a cosmetic composition, dispersion stability of the powder throughout the entire cosmetic composition can be improved and a cosmetic composition that is stable over time can be obtained.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range from 0.1 to 50 μm. Additionally, a silicone elastomer powder having spherical primary particles can be preferably compounded. The silicone elastomer that constitutes the silicone elastomer powder preferably has a hardness of no higher than 80 and more preferably no higher than 65, when measured using a type A durometer in accordance with the "Method for measuring the hardness of vulcanized rubber and thermoplastic rubber" described in JIS K 6253.

Of these silicone elastomer powders, specific examples of silicone elastomer spherical powders are the same as those recited in paragraph 0168 of Patent Document 5 (WO2011/049248, filed by the present applicant), and as recited in paragraphs 0150 to 0152 of the same publication, and may be a silicone elastomer powder that has been subjected to any type of water-repellent treatment.

The mixture of the co-modified organopolysiloxane (A) and the powder or coloring agent (B) is a form in which the powder is dispersed in the co-modified organopolysiloxane, and a compounded amount of the powder in the mixture is not particularly limited but is preferably in a range from 50 to 99 wt. % and more preferably in a range from 80 to 90 wt. % of the entire mixture.

(C) Oil Agent

The oil agent used in the powder in oil dispersion and the like according to the present invention preferably is one or more oil agent selected from a silicone oil, a nonpolar organic compound, and a low polarity organic compound that are liquid from 5 to 100° C. A hydrocarbon oil and a fatty acid ester oil are preferable as the nonpolar organic compound and the low polarity organic compound. These oil agents are components that are widely used, particularly as base materials of make-up cosmetic composition. These oil agents may be thickened or gelled after being combined with one or two or more types of commonly known vegetable oils and fats, animal oils and fats, higher alcohols, liquid triglyceride fatty acids, artificial sebums, or fluorine-based oils. The co-modified organopolysiloxane also displays superior dispersibility in these non-silicone-based oil agents and, therefore the hydrocarbon oil and the fatty acid ester oil can be stably compounded in a cosmetic composition and moisturizing characteristics imparted by these non-silicone-based oil agents can be maintained. Thus, the co-modified organopolysiloxane can improve stability over time of these non-silicone-based oil agent in a cosmetic composition.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are the same as those recited in paragraphs 0130 to 0135, paragraph 0206, and the like of Patent Document 5 (WO2011/049248, filed by the present applicant). Examples of the fluorine-based oil include perfluoropolyether, perfluorodecalin, perfluorooctane, and the like.

A compounded amount of the oil agent in the powder in oil dispersion of the present invention is not particularly limited but is preferably in a range from 0.1 to 50 wt. % and more preferably in a range from 0.5 to 25 wt. % in the raw material for use in cosmetic compositions.

The co-modified organopolysiloxane and the powder composition or the powder in oil dispersion comprising the co-modified organopolysiloxane can be suitably used as a preparation for external use, particularly for a cosmetic composition or a cosmetic raw material. Such preparations for external use, particularly cosmetic compositions or cosmetic raw materials are within the scope of the present invention.

Particularly, the co-modified organopolysiloxane and the powder composition or the powder in oil dispersion comprising the co-modified organopolysiloxane can be advantageously used as a make-up cosmetic composition raw material. Such make-up cosmetic compositions comprising the co-modified organopolysiloxane and the powder composition or the powder in oil dispersion comprising the co-modified organopolysiloxane particularly are within the scope of the preferable embodiments of the present invention.

Water (D) can be further compounded in the cosmetic composition of the present invention and, thereby, the cosmetic composition of the present invention may take the form of an oil-in-water emulsion or a water-in-oil emulsion. In this case, the cosmetic composition of the present invention displays superior emulsion stability and sensation during use. Preparation of a hydrous cosmetic composition and an emulsion cosmetic composition is the same as recited in paragraphs 0128 to 0146 and the like of Patent Document 5 (WO2011/049248, filed by the present applicant).

A uniformly soluble product (emulsion premix) that is the cosmetic raw material is formed by mixing the co-modified organopolysiloxane with the powder and the oil agent optionally in the presence of ethanol or a similar alcohol. The premix is mixed with water using the device described above. Thus, a cosmetic composition in the form of a uniform oil-in-water emulsion or water-in-oil emulsion can be produced.

The cosmetic composition of the present invention can further comprise (E) other surfactants. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those recited in paragraphs 0162, 0163, 0195 to 0201, and the like of Patent Document 5 (WO2011/049248, filed by the present applicant). The co-modified organopolysiloxane used in the present invention has a hydrophilic moiety and a hydrophobic moiety in the molecule and, therefore, has functionality as a dispersing agent. Thus, in cases where used in combination with a silicone-based nonionic surfactant, the component (A) functions as an aid to enhance the stability of the nonionic surfactant and may improve overall stability of the formulation. Particularly, the co-modified organopolysiloxane is preferably used in combination with polyoxyalkylene-modified silicones, polyglyceryl-modified silicones, and glyceryl-modified silicones. Moreover, the silicone-based nonionic surfactants described above in which an alkyl branch, a straight chain silicone branch, a siloxane dendrimer branch, or the like is provided with the hydrophilic group can be advantageously used.

Depending on the purpose thereof, the cosmetic composition of the present invention can comprise one or two or more polyhydric alcohols and/or lower monohydric alcohols as a component (F). These alcohols are the same as those recited in paragraphs 0159, 0160, and the like of Patent Document 5 (WO2011/049248, filed by the present applicant).

Depending on the purpose thereof, the cosmetic composition of the present invention can comprise one or two or more inorganic salts and/or organic salts as a component (G). These salts are the same as those recited in paragraph 0161 and the like of Patent Document 5 (WO2011/049248, filed by the present applicant).

Depending on the purpose thereof, the cosmetic composition of the present invention can comprise at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (H). These silicone-based components are the same as those recited in paragraphs 0161 to 0193 and the like of Patent Document 5 (WO2011/049248, filed by the present applicant). Examples of the component (H) other than those recited in Patent Document 5 include (H-1): a silicone polyester elastomer gel described in WO2007/109240 and WO2009/006091 in which compatibility with various components is enhanced and stable thickening effects are displayed as a result of introducing a polyoxypropylene group. Examples of commercially available products thereof include Dow Corning EL-8050 ID SILICONE ORGANIC ELASTOMER BLEND, Dow Corning EL-8051 IN SILICONE ORGANIC ELASTOMER BLEND, Dow Corning EL-7040 HYDRO ELASTOMER BLEND; and (H-2): PITUITOUS SILICONE FLUIDS described in WO2011/028765 and WO2011/028770. At least one type selected from these products can be used depending on the purpose of the cosmetic composition of the present invention. Furthermore, the liquid and slightly-crosslinkable organopolysiloxane proposed in Japanese Patent Application No. 2010-289722 and the domestic priority claimed therefrom (filed by the present applicant) can be used in the present invention.

The cosmetic composition of the present invention can, depending on the purpose of the cosmetic composition, comprise one or two or more water-soluble polymers as a component (J). These water-soluble polymers are the same as those recited in paragraph 0201 and the like of Patent Document 5 (WO2011/049248, filed by the present applicant).

Depending on the purpose thereof, the cosmetic composition of the present invention can comprise one or two or more ultraviolet light blocking components as a component (K). These ultraviolet light blocking components are the same as the organic and inorganic ultraviolet light blocking components recited in paragraphs 0202 to 0204 and the like in Patent Document 5 (WO2011/049248, filed by the present applicant). However, ultraviolet light blocking components that can be particularly preferably used include at least one type selected from the group consisting of microparticle titanium oxide, microparticle zinc oxide, paramethoxy cinnamic acid 2-ethylhexyl, 4-tert-butyl-4'-methoxydibenzoylmethane, diethylamino hydroxybenzoyl hexyl benzoate, benzotriazole-based UV absorber, 2,4,6-tris[4-(2-ethylhexyloxycarbonyl)anilino]1,3,5-triazine (INCI: ethylhexyl triazone), 2,4-bis-6-(4-methoxyphenyl)-1,3,5-triazine (INCI: bis-ethylhexyloxyphenol methoxyphenyl triazine, trade designation: Tinosorb® S), and similar triazine-based UV absorbers. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

In the cosmetic composition of the present invention, by using the raw material for use in cosmetic compositions comprising the co-modified organopolysiloxane and the ultraviolet light blocking component together, the ultraviolet light blocking component can be stably dispersed in the cosmetic composition and the tactile sensation and the storage stability of the entire cosmetic composition can be improved. Therefore, superior UV blocking capacity can be imparted to the cosmetic composition.

In the cosmetic composition of the present invention, a total compounded amount of the ultraviolet light blocking component with respect to the entire cosmetic composition is in a range from 0.1 to 40.0 wt % (mass %), and more preferably in a range from 0.5 to 15.0 wt. % (mass %).

Various components other than the components described above can be used in the cosmetic composition of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These cosmetic product-use optional components are the same as those recited in paragraphs 0207, 0208, 0220 to 0228, and the like of Patent Document 5 (WO2011/049248, filed by the present applicant).

Additionally, in cases where the cosmetic composition according to the present invention is an anti-perspirant, or depending on the purpose of the cosmetic composition, the cosmetic composition can contain an anti-perspiration active component and/or a deodorant agent. These anti-perspirants and deodorant agents are the same as those recited in paragraphs 0209 to 0219 and the like of Patent Document 5 (WO2011/049248, filed by the present applicant). Likewise, in cases where the cosmetic composition according to the present invention is an anti-perspirant composition, the preparation, methods of use, and the like of the various anti-perspirant compositions are the same as those recited in paragraphs 0234 to 0275 and the like of Patent Document 5 (WO2011/049248, filed by the present applicant).

The preparation for external use according to the present invention is not particularly limited, provided that it is a composition for application to the human body as a cosmetic composition or a medicament. Specific examples of products that the cosmetic composition of the present invention can be used for include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The types, forms, and containers of the preparation for external use according to the present invention are the same as those recited in paragraphs 0230 to 0233 and the like of Patent Document 5 (WO2011/049248, filed by the present applicant), but the co-modified organopolysiloxane is particularly useful as a raw material for various make-up cosmetic compositions. Additionally, the cosmetic composition according to the present invention is most advantageous as a make-up cosmetic composition comprising the co-modified organopolysiloxane (A), the powder or colorant (B), and the silicone oil, nonpolar organic compound, or low polarity organic compound (C) that is liquid from 5 to 100° C.

Examples of the make-up cosmetic composition include foundations, liquid foundations, oil-based foundations, makeup bases, powders, face powders, lipsticks, lip creams, muddy colored lipsticks or rouges, lip glosses, eye shadows, eye liners, eye creams, eyebrow pencils, eyelash cosmetic products, eyebrow pencils, eyebrow blushes, mascaras, blushers, cheek cosmetics (cheek color, cheek rouge), manicures, pedicures, nail colors, nail lacquers, enamel removers, nail polishes, and the like.

EXAMPLES

Hereinafter, the present invention is described in detail with reference to Practical Examples and Comparative Examples, but it should be understood that the present invention is not limited to these Practical Examples. In the examples, viscosity (kinetic viscosity) is a value measured at 25° C. In the compositional formulae below, "M" represents a $Me_3SiO$ group (or a $Me_3Si$ group), "D" represents a $Me_2SiO$ group, "$D^H$" represents a MeHSiO group, and "$D^R$" represents units in which a methyl group in "D" is modified by any substituent. Additionally, a xylitol monoallyl ether and a xylitol residue recited in the Practical Examples and Reference Example 2 below are the raw material and the functional group described in the present specification. More specifically, the xylitol monoallyl ether is a raw material comprising xylitol monoallyl ethers represented by structural formula: $CH_2{=}CH{-}CH_2{-}OCH_2[CH(OH)]_3CH_2OH$, and structural formula: $CH_2{=}CH{=}CH_2{-}OCH\{CH(OH)CH_2OH\}_2$ at a matter weight ratio of 9:1. A xylitol residue corresponding to this raw material represented by the formula: $-C_3H_6{-}OCH_2[CH(OH)]_3CH_2OH$, or $-C_3H_6{-}OCH\{CH(OH)CH_2OH\}_2$ is introduced into the co-modified silicone of the present invention at the same matter weight ratio.

Practical Example 1

Synthesis of Co-Modified Organopolysiloxane Compound P1

113.7 g of a methylhydrogenpolysiloxane expressed by average composition formula $MD_{15}D^H{}_3M$, 75.1 g of a tristrimethylsiloxyvinylsilane, 11.2 g of a xylitol monoallyl ether, and 11.2 g of isopropyl alcohol (IPA) were placed in a reaction vessel. The mixture was heated to 70° C. while agitating under a stream of nitrogen. Then, 0.100 g of a platinum catalyst was added and the mixture was reacted for 10 hours. Completion of the reaction was confirmed via an alkali decomposition gas generation method (i.e. the remaining Si—H groups were decomposed using a KOH ethanol/water solution, and the reaction rate is calculated from the volume of the produced hydrogen gas). The reaction liquid was heated at 120° C. under reduced pressure in order to remove the low-boiling components via distillation and, thereafter the resulting product was subjected to filtration. Thus, a novel xylitol co-modified organopolysiloxane having a siloxane dendron structure expressed by the average composition formula $MD_{15}D^{R1}{}_{2.4}D^{R2}{}_{0.6}M$ was obtained. In this formula, $R^1$ and $R^2$ have the structures described below.

$R^1{=}{-}C_2H_4Si(OSiMe_3)_3$ $R^2$ is a hydrophilic group expressed by $—C_3H_6O—X$, wherein X is the xylitol residue.

This product was a yellow viscous transparent liquid.

Practical Example 2

Synthesis of Co-Modified Organopolysiloxane Compound P2

108.6 g of a methylhydrogenpolysiloxane expressed by the average composition formula $MD_{15}D^H{}_3M$, 71.7 g of a tristrimethylsiloxyvinylsilane, 19.7 g of a polyglycerine monoallyl ether, and 19.7 g of isopropyl alcohol (IPA) were placed in a reaction vessel. The mixture was heated to 70° C. while agitating under a stream of nitrogen. Then, 0.100 g of a platinum catalyst was added and the mixture was reacted for 10 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{15}D^{R1}{}_{2.4}D^{R3}{}_{0.6}M$ was obtained.

Here the polyglycerine monoallyl ether is synthesized by ring-opening polymerizing 3 molar equivalents of glycidol with 1 mole of a glycerin monoallyl ether. Moreover, the glycerin monoallyl ether has two hydroxyl groups that can both react with the glycidol and, thus, the polyglycerin moiety comprises not only a straight chain structure, but also a branched structure. In this formula, $R^1$ is synonymous with that described above and $R^3$ has the structure described below.

$R^3$ is a hydrophilic group expressed by $—C_3H_6O—X$, wherein X is a tetraglycerin moiety.

This product was a light yellow viscous transparent liquid.

Practical Example 3

Synthesis of Co-Modified Organopolysiloxane Compound P3

146.9 g of a methylhydrogenpolysiloxane expressed by the average composition formula $MD_{33}D^H{}_3M$, 40.2 g of a tristrimethylsiloxyvinylsilane, 12.9 g of a diglycerin monoallyl ether, and 12.9 g of isopropyl alcohol (IPA) were placed in a reaction vessel. The mixture was heated to 70° C. while agitating under a stream of nitrogen. Then, 0.100 g of a platinum catalyst was added and the mixture was reacted for 10 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{33}D^{R1}{}_2D^{R4}{}_1M$ was obtained.

In this formula, $R^1$ is synonymous with that described above and $R^4$ has the structure described below.

$R^4$ is a hydrophilic group expressed by $—C_3H_6O—X$, wherein X is a diglycerin moiety.

This product was a light yellow viscous transparent liquid.

Practical Example 4

Synthesis of Co-Modified Organopolysiloxane Compound P4

113.2 g of a methylhydrogenpolysiloxane expressed by the average composition formula $MD_{15}D^H{}_3M$, 74.8 g of a tristrimethylsiloxyvinylsilane, 12.0 g of a diglycerin monoallyl ether, and 12.0 g of isopropyl alcohol (IPA) were placed in a reaction vessel. The mixture was heated to 70° C. while agitating under a stream of nitrogen. Then, 0.100 g of a platinum catalyst was added and the mixture was reacted for 10 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{15}D^{R1}{}_{2.4}D^{R4}{}_{0.6}M$ was obtained.

In this formula, $R^1$ and $R^4$ are synonymous with those described above.

This product was a light yellow viscous transparent liquid.

Practical Example 5

Synthesis of Co-Modified Organopolysiloxane Compound P5

148.7 g of a methylhydrogenpolysiloxane expressed by the average composition formula $MD_{69}D^H{}_5M$, 46.6 g of a tristrimethylsiloxyvinylsilane, 4.8 g of a glycerin monoallyl ether, and 4.8 g of isopropyl alcohol (IPA) were placed in a reaction vessel. The mixture was heated to 70° C. while agitating under a stream of nitrogen. Then, 0.100 g of a platinum catalyst was added and the mixture was reacted for 10 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{69}D^{R1}{}_4D^{R5}{}_1M$ was obtained.

In this formula, $R^1$ is synonymous with that described above and $R^5$ has the structure described below.

$$R^5{=}—C_3H_6O—CH_2CH(OH)CH_2OH$$

This product was a light yellow viscous transparent liquid.

Practical Example 6

Synthesis of Co-Modified Organopolysiloxane Compound P6

67.91 g of a methylhydrogenpolysiloxane expressed by the average composition formula $MD_{30}D^H{}_6M$, 16.03 g of a tristrimethylsiloxyvinylsilane, 7.7 g of a diglycerin monoallyl ether, 8.36 g of 1-octene, and 20 g of toluene were placed in a reaction vessel. The mixture was heated to 70° C. while agitating under a stream of nitrogen. Then, 0.100 g of a platinum catalyst was added and the mixture was reacted for 16 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{30}D^{R1}{}_2D^{R4}{}_1D^{R6}{}_3M$ was obtained.

In this formula, $R^1$ and $R^4$ are synonymous with those described above and $R^6$ has the structure described below.

$R^6$=—$C_8H_{17}$

This product was a light yellow transparent liquid.

Practical Example 7

Synthesis of Co-Modified Organopolysiloxane Compound P7

56.59 g of a methylhydrogenpolysiloxane expressed by the average composition formula $MD_{30}D^{H}{}_6M$, 13.73 g of a tristrimethylsiloxyvinylsilane, 4.61 g of a diglycerin monoallyl ether, 25.07 g of 1-dodecene, and 20 g of toluene were placed in a reaction vessel. The mixture was heated to 70° C. while agitating under a stream of nitrogen. Then, 0.50 g of a platinum catalyst was added and the mixture was reacted for 20 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{30}D^{R1}{}_2D^{R4}{}_1D^{R7}{}_3M$ was obtained.

In this formula, $R^1$ and $R^4$ are synonymous with those described above and $R^7$ has the structure described below.

$R^7$=—$C_{12}H_{25}$

This product was a brown transparent liquid.

Comparative Example 1

Synthesis of Co-Modified Organopolysiloxane Compound R1

133.18 g of a methylhydrogenpolysiloxane expressed by the average composition formula $MD_{18}D^{H}{}_1M$, 38.95 g of a polyglycerine monoallyl ether, and 78 g of isopropyl alcohol (IPA) were placed in a reaction vessel. The mixture was heated to 70° C. while agitating under a stream of nitrogen. Then, 0.086 g of a platinum catalyst was added and the mixture was reacted for 8 hours. Completion of the reaction was confirmed via an alkali decomposition gas generation method. The reaction liquid was heated at 120° C. under reduced pressure in order to remove the low-boiling components via distillation and, thereafter the resulting product was subjected to filtration. Thus, a novel glycerin co-modified organopolysiloxane having a siloxane dendron structure expressed by the average composition formula $MD_{18}D^{R3}{}_1M$ was obtained.

In this formula, $R^3$ is synonymous with that described above. This product was a ochre-colored viscous liquid. Additionally, the kinetic viscosity thereof exceeded 1,500 mPa·s.

Synthesis of Co-Modified Organopolysiloxane Compounds R2 and R3

Co-modified organopolysiloxane compounds R2 and R3 were synthesized based on the Practical Examples of Patent Document 5 for the purpose of comparison with the co-modified organopolysiloxane recited in Patent Document 5 (WO2011/049248, filed by the present applicant). These compounds were viscous liquids having kinetic viscosities that exceeded 1,500 mPa·s.

Synthesis of Co-Modified Organopolysiloxane Compound R2

160.9 g of a methylhydrogenpolysiloxane expressed by the average composition formula $MD_{45}D^{H}{}_2M$, 18.6 g of a tristrimethylsiloxyvinylsilane, 20.5 g of a polyglycerine monoallyl ether, and 200 g of isopropyl alcohol (IPA) were placed in a reaction vessel. The mixture was heated to 70° C. while agitating under a stream of nitrogen. Then, 0.067 g of a platinum catalyst was added and the mixture was reacted for 3 hours. Completion of the reaction was confirmed via an alkali decomposition gas generation method. The reaction liquid was heated at 120° C. under reduced pressure in order to remove the low-boiling components via distillation. Thus, a novel glycerin co-modified organopolysiloxane having a siloxane dendron structure expressed by the average composition formula $MD_{45}D^{R1}{}_1D^{R3}{}_1M$ was obtained.

In this formula, $R^1$ and $R^3$ are synonymous with those described above.

Synthesis of Co-Modified Organopolysiloxane Compound R3

171.9 g of a methylhydrogenpolysiloxane expressed by the average composition formula $MD_{45}D^{H}{}_2M$, 19.9 g of a tristrimethylsiloxyvinylsilane, 8.2 g of a glycerin monoallyl ether, and 60 g of isopropyl alcohol (IPA) were placed in a reaction vessel. The mixture was heated to 70° C. while agitating under a stream of nitrogen. Then, 0.04 g of a platinum catalyst was added and the mixture was reacted for 2 hours. Completion of the reaction was confirmed via an alkali decomposition gas generation method. The reaction liquid was heated at 120° C. under reduced pressure in order to remove the low-boiling components via distillation. Thus, a novel glycerin co-modified organopolysiloxane having a siloxane dendron structure expressed by the average composition formula $MD_{45}D^{R1}{}_1D^{R5}{}_1M$ was obtained.

In this formula, $R^1$ and $R^5$ are synonymous with those described above.

<Organopolysiloxane Compound R4>

The organopolysiloxane compound R4 used in the comparison experiments was the product described below. Kinetic viscosity of the organopolysiloxane was less than 1,500 mPa·s and HLB was 4.0.

ES5612: Polyether-modified silicone (trade designation: ES5612, manufactured by Dow Corning Toray Co., Ltd.)

The average composition formulae, HLB, and viscosity of the co-modified organopolysiloxane compounds P1 to P7 according to the present invention, and Comparative co-modified organopolysiloxane compounds R1 to R3 according to the comparative examples, which were synthesized according to the methods described above, are shown in Table 1.

TABLE 1

| | Average composition formula | HLB | Viscosity (mPa · s) |
|---|---|---|---|
| Co-modified organopolysiloxane | | | |
| P1 | $MD_{15}D^{R1}_{2.4}D^{R2}_{0.6}M$ | 1.0 | 340 |
| P2 | $MD_{15}D^{R1}_{2.4}D^{R3}_{0.6}M$ | 2.0 | 260 |
| P3 | $MD_{33}D^{R1}_{2}D^{R4}_{1}M$ | 0.9 | 670 |
| P4 | $MD_{15}D^{R1}_{2.4}D^{R4}_{0.6}M$ | 1.1 | 240 |
| P5 | $MD_{69}D^{R1}_{4}D^{R5}_{1}M$ | 0.3 | 470 |
| P6 | $MD_{30}D^{R1}_{2}D^{R4}D^{R6}_{3}M$ | 0.8 | 1220 |
| P7 | $MD_{30}D^{R1}_{2}D^{R4}D^{R7}_{3}M$ | 0.8 | 1270 |
| Comparative organopolysiloxane | | | |
| R1 | $MD_{18}D^{R3}_{1}M$ | 3.3 | >1,500 |
| R2 | $MD_{45}D^{R1}_{1}D^{R3}_{1}M$ | 1.5 | >1,500 |
| R3 | $MD_{45}D^{R1}_{1}D^{R5}_{1}M$ | 0.5 | >1,500 |
| R4 | — | 4.0 | 900 |

In the tables, the structures and types of the functional groups are as follows.

$R^{1=-c}{}_2H_4Si(OSiMe_3)_3$ $R^2$ is a hydrophilic group expressed by —$C_3H_6O$—X, wherein X is the xylitol residue.

$R^3$ is a hydrophilic group expressed by —$C_3H_6O$—X, wherein X is a polyglycerine moiety.

$R^4$ is a hydrophilic group expressed by —$C_3H_6O$—X, wherein X is a diglycerin moiety.

$R^5$=—$C_3H_6O$—$CH_2CH(OH)CH_2OH$ $R^6$=—$C_8H_{17}$ $R^7$=—$C_{12}H_{25}$

Evaluation of Dispersion Stability

Slurry-like microparticle dispersions were prepared according to the formulations and preparation methods shown in Dispersion Preparation 1 to Dispersion Preparation 8 below. These microparticle dispersions were then evaluated from the standpoints of dispersion characteristics and change in viscosity with time. 1,000 mPas was set as the standard for the viscosity of the slurries and those that had viscosities that were lower than 1,000 mPas were considered to be “low viscosity” and those that were higher than 1,000 mPas were considered to be “high viscosity”. Additionally, in cases where the slurry gelified after agitating using a paint shaker in the stage of producing the slurry, the product was labeled “slurry production impossible”. The results are shown in Table 2. The components used in the preparation of each dispersion are as follows.

(1) Microparticle powder: Fine particulate titanium oxide

Trade designation: MTY-02 (manufactured by Tayca Corporation)

Particle size: 10 nm (2) Microparticle powder: Fine particulate zinc oxide

Trade designation: FINEX-30S-LPT (manufactured by Sakai Chemical Industry Co., Ltd.)

Particle size: 35 nm (3) Dispersing medium: Decamethyl cyclopentasiloxane

Trade designation: DC245 (manufactured by Dow Corning Toray Co., Ltd.)

Practical Example: Preparation of Dispersion 1

A slurry-like dispersion (TP1) was produced by mixing 20 g of the fine particulate titanium oxide, 5 g of the co-modified organopolysiloxane (P1) of Practical Example 1, and 25 g of a decamethyl cyclopentasiloxane; adding 200 g of zirconia beads (Φ0.8 mm) thereto; and mixing the mixture using a paint shaker (PAINT SHAKER, manufactured by Asada Iron Works Co., Ltd.) for 15 hours.

Practical Example: Preparation of Dispersion 2

A slurry-like dispersion (TP2) was produced the same as in the preparation of dispersion 1, except that the co-modified organopolysiloxane (P2) of Practical Example 2 was used in place of the co-modified organopolysiloxane (P1) of Practical Example 1.

Practical Example: Preparation of Dispersion 3

A slurry-like dispersion (TP3) was produced the same as in the preparation of dispersion 1, except that the co-modified organopolysiloxane (P3) of Practical Example 3 was used in place of the co-modified organopolysiloxane (P1) of Practical Example 1.

Practical Example: Preparation of Dispersion 4

A slurry-like dispersion (TP4) was produced the same as in the preparation of dispersion 1, except that the co-modified organopolysiloxane (P4) of Practical Example 4 was used in place of the co-modified organopolysiloxane (P1) of Practical Example 1.

Practical Example: Preparation of Dispersion 5

A slurry-like dispersion (TP5) was produced the same as in the preparation of dispersion 1, except that the co-modified organopolysiloxane (P5) of Practical Example 5 was used in place of the co-modified organopolysiloxane (P1) of Practical Example 1.

Comparative Example: Preparation of Dispersion 6

A slurry-like dispersion (TP6) was produced the same as in the preparation of dispersion 1, except that the co-modified organopolysiloxane (P6) of Practical Example 6 was used in place of the co-modified organopolysiloxane (P1) of Practical Example 1.

Comparative Example: Preparation of Dispersion 7

A slurry-like dispersion (TP7) was produced the same as in the preparation of dispersion 1, except that the co-modified organopolysiloxane (P7) of Practical Example 7 was used in place of the co-modified organopolysiloxane (P1) of Practical Example 1.

Comparative Example: Preparation of Dispersion 8

A slurry-like dispersion (TR1) was produced the same as in the preparation of dispersion 1, except that the co-modified organopolysiloxane (R1) of Comparative Example 1 was used in place of the co-modified organopolysiloxane (P1) of Practical Example 1.

Comparative Example: Preparation of Dispersion 9

A slurry-like dispersion (TR2) was produced the same as in the preparation of dispersion 1, except that the co-modified organopolysiloxane (R2) of Comparative Example 2 was used in place of the co-modified organopolysiloxane (P1) of Practical Example 1.

Comparative Example: Preparation of Dispersion 10

A slurry-like dispersion (TR3) was produced the same as in the preparation of dispersion 1, except that the co-modified organopolysiloxane (R3) of Comparative Example 3 was used in place of the co-modified organopolysiloxane (P1) of Practical Example 1.

Comparative Example: Preparation of Dispersion 11

A slurry-like dispersion (TR4) was produced the same as in the preparation of dispersion 1, except that the co-modified organopolysiloxane (R4) of Comparative Example 4 was used in place of the co-modified organopolysiloxane (P1) of Practical Example 1.

Practical Example: Preparation of Dispersion 12

A slurry-like dispersion (ZP1) was produced by mixing 30 g of the fine particulate zinc oxide, 2.5 g of the co-modified organopolysiloxane (P1) of Practical Example 1, and 17.5 g of a decamethyl cyclopentasiloxane; adding 200 g of zirconia beads (00.8 mm) thereto; and mixing the mixture using a paint shaker for 15 hours.

Practical Example: Preparation of Dispersion 13

A slurry-like dispersion (ZP2) was produced the same as in the preparation of dispersion 12, except that the co-modified organopolysiloxane (P2) of Practical Example 2 was used in place of the co-modified organopolysiloxane (P1) of Practical Example 1.

Practical Example: Preparation of Dispersion 14

A slurry-like dispersion (ZP3) was produced the same as in the preparation of dispersion 12, except that the co-modified organopolysiloxane (P3) of Practical Example 3 was used in place of the co-modified organopolysiloxane (P1) of Practical Example 1.

Practical Example: Preparation of Dispersion 15

A slurry-like dispersion (ZP4) was produced the same as in the preparation of dispersion 12, except that the co-modified organopolysiloxane (P4) of Practical Example 4 was used in place of the co-modified organopolysiloxane (P1) of Practical Example 1.

Practical Example: Preparation of Dispersion 16

A slurry-like dispersion (ZP5) was produced the same as in the preparation of dispersion 12, except that the co-modified organopolysiloxane (P5) of Practical Example 5 was used in place of the co-modified organopolysiloxane (P1) of Practical Example 1.

Comparative Example: Preparation of Dispersion 17

A slurry-like dispersion (ZP6) was produced the same as in the preparation of dispersion 12, except that the co-modified organopolysiloxane (P6) of Practical Example 6 was used in place of the co-modified organopolysiloxane (P1) of Practical Example 1.

Comparative Example: Preparation of Dispersion 18

A slurry-like dispersion (ZP7) was produced the same as in the preparation of dispersion 12, except that the co-modified organopolysiloxane (P7) of Practical Example 7 was used in place of the co-modified organopolysiloxane (P1) of Practical Example 1.

Comparative Example: Preparation of Dispersion 19

A slurry-like dispersion (ZR2) was produced the same as in the preparation of dispersion 12, except that the co-modified organopolysiloxane (R1) of Comparative Example 1 was used in place of the co-modified organopolysiloxane (P1) of Practical Example 1.

Comparative Example: Preparation of Dispersion 20

A slurry-like dispersion (ZR3) was produced the same as in the preparation of dispersion 12, except that the co-modified organopolysiloxane (R2) of Comparative Example 2 was used in place of the co-modified organopolysiloxane (P1) of Practical Example 1.

Comparative Example: Preparation of Dispersion 21

A slurry-like dispersion (ZR4) was produced the same as in the preparation of dispersion 12, except that the co-modified organopolysiloxane (R3) of Comparative Example 3 was used in place of the co-modified organopolysiloxane (P1) of Practical Example 1.

Comparative Example: Preparation of Dispersion 22

A slurry-like dispersion (ZR5) was produced the same as in the preparation of dispersion 12, except that the co-modified organopolysiloxane (R4) of Comparative Example 4 was used in place of the co-modified organopolysiloxane (P1) of Practical Example 1.

TABLE 2

| Sample | Titanium oxide slurry | Evaluation | Zinc oxide slurry | Evaluation |
|---|---|---|---|---|
| P1 | TP1 | ○○ | ZP1 | ○○ |
| P2 | TP2 | ○○ | ZP2 | ○○ |
| P3 | TP3 | ○○ | ZP3 | ○○ |
| P4 | TP4 | ○○ | ZP4 | ○Δ |
| P5 | TP5 | ○○ | ZP5 | ○○ |
| P6 | TP6 | ○○ | ZP6 | ○○ |
| P7 | TP7 | ○Δ | ZP7 | Δ○ |
| R1 | TR1 | ΔΔ | ZR1 | x— |
| R2 | TR2 | ○Δ | ZR2 | x— |
| R3 | TR3 | ΔΔ | ZR3 | x— |
| R4 | TR4 | ○Δ | ZR4 | x— |

Evaluation standards are as follows.
○○: Low viscosity slurry producible, no increase in viscosity with time
○Δ : Low viscosity slurry producible, increase in viscosity with time
Δ○: High viscosity slurry producible, reduction in viscosity with time
ΔΔ: High viscosity slurry producible, increase in viscosity with time
x—: Slurry production impossible As shown in Table 2, with the novel co-modified organopolysiloxanes P1 to P7 according to the present invention, powder in oil dispersions (slurries) were producible regardless of whether the powder was titanium oxide or zinc oxide. In contrast, with the comparative compounds R1 to R4 and particularly in cases where the microparticle zinc oxide was used, even with the comparative co-modified organopolysiloxanes R2 and R3 that had structures similar to the co-modified organopolysiloxanes P3 and P5 according to the present invention, slurries could not be produced under the same conditions as the co-modified organopolysiloxanes according to the present invention and a prominent difference in performance as a powder treatment agent was observed. Additionally, when the titanium oxide was used, even in the case of the comparative organopolysiloxane, while a slurry could be produced, overall performance was inferior compared to the powder in oil dispersions using the novel co-modified organopolysiloxane according to the present invention. That is, for example, as seen in a comparison of the dispersion results of ZP3 and ZP5, and ZR2 and ZR3, viscosity increased with time, the viscosity of the slurries increased, and the like. One cause of dispersibility in zinc oxide slurries being significantly worse than in titanium oxide slurries is because the ratio of the powder in the formulation is greater in zinc oxide slurries than in titanium oxide slurries. This indicates that efficiency when producing the slurries greatly affects performance. That is, the viscosity of the present invention products is lower than that of the comparative products and, as a result, it is thought that the slurries were producible because efficient agitation was possible even when zinc oxide was used.

Formulation Examples

Hereinafter, examples are given based on specific formulations for the cosmetic composition of the present invention, but it is understood that the types and formulations of the cosmetic composition of the present invention are not limited to the types and formulations described in these examples. Note that in the formulations, "part(s)" refers to parts by weight (mass).

Formulation Example 1: Liquid foundation (W/O type)
Formulation Example 2: Liquid foundation (W/O type)
Formulation Example 3: Liquid foundation (W/O type)
Formulation Example 4: Sunscreen cream (W/O type)
Formulation Example 5: Sunscreen (shaking type)
Formulation Example 6: Base cream
Formulation Example 7: Rouge
Formulation Example 8: Liquid rouge
Formulation Example 9: Lipstick
Formulation Example 10: Lip gloss
Formulation Example 11: Eye shadow
Formulation Example 12: Mascara Formulation Example 1: Liquid foundation (W/O type)

| Components | | |
|---|---|---|
| 1. | Decamethyl cyclopentasiloxane | 30 parts |
| 2. | Isotridecyl isononanoate | 3 parts |
| 3. | Glyceryl tricaprinate/tricaprylate | 2 parts |
| 4. | Polyether-modified silicone (see note 1) | 1.5 parts |
| 5. | Co-modified organopolysiloxane P7 | 0.5 parts |
| 6. | Organo-modified clay mineral (Bentone 38V) | 1.5 parts |
| 7. | Octyl methoxycinnamate | 5 parts |
| 8. | Silicone treated titanium oxide | 8.5 parts |
| 9. | Silicone treated red Iron oxide | 0.4 parts |
| 10. | Silicone treated yellow iron oxide | 1 part |
| 11. | Silicone treated black iron oxide | 0.1 parts |
| 12. | Decamethyl cyclopentasiloxane, dimethicone crosspolymer (see note 2) | 2 parts |

-continued

Formulation Example 1: Liquid foundation (W/O type)

| Components | | |
|---|---|---|
| 13. | 1,3-butylene glycol | 5 parts |
| 14. | Glycerin | 3 parts |
| 15. | Sodium chloride | 0.5 parts |
| 16. | Preservative | q.s. |
| 17. | Purified water | Remainder |
| 18. | Perfume | q.s. |

Note 1:
ES-5612, manufactured by Dow Corning Toray Co., Ltd. was used.
Note 2:
DC9040, manufactured by Dow Corning was used.

Manufacturing Method

Step 1: Agitate and mix components 1, 4, 6, 7, and 12.

Step 2: Knead and mix components 2, 3, and 8 to 11 using a three-roller mill.

Step 3: Add the mixture obtained in step 2 to the mixture obtained in step 1 while agitating. Agitate and mix further.

Step 4: Add an aqueous phase in which components 13 to 18 are uniformly dissolved to the mixture obtained in step 3 and emulsify, and fill a container with the emulsion to obtain the product.

When used, the obtained W/O type liquid foundation had superior emulsion stability and superior moisture resistance and cosmetic durability. Skin imperfections and wrinkles were concealed and spreadability and adhesion was superior.

Formulation Example 2: Liquid foundation (W/O type)

| Components | | |
|---|---|---|
| 1. | Isododecane | 20 parts |
| 2. | Isohexadecane | 10 parts |
| 3. | Isotridecyl isononanoate | 3 parts |
| 4. | Glyceryl tricaprinate/tricaprylate | 2 parts |
| 5. | Polyether-modified silicone (see note 1) | 1.5 parts |
| 6. | Co-modified organopolysiloxane P6 | 0.5 parts |
| 7. | Organo-modified clay mineral (Bentone 38V) | 1.5 parts |
| 8. | Octyl methoxycinnamate | 5 parts |
| 9. | Octylsilane treated titanium oxide | 8.5 parts |
| 10. | Octylsilane treated red iron oxide | 0.4 parts |
| 11. | Octylsilane treated yellow iron oxide | 1 part |
| 12. | Octylsilane treated black iron oxide | 0.1 parts |
| 13. | Dimethicone, dimethicone crosspolymer (see note 2) | 2 parts |
| 14. | Copolymer of Isododecane and (acrylates/polytrimethylsiloxy methacrylate) (see note 3) | 1 part |
| 15. | Trimethylsiloxysilicate | 1 part |
| 16. | 1,3-butylene glycol | 5 parts |
| 17. | Glycerin | 3 parts |
| 18. | Sodium chloride | 0.5 parts |
| 19. | Preservative | q.s. |
| 20. | Purified water | Remainder |
| 21. | Perfume | q.s. |

Note 1:
ES-5300, manufactured by Dow Corning Toray Co., Ltd. was used.
Note 2:
DC9045, manufactured by Dow Corning was used.
Note 3:
FA-4002ID, manufactured by Dow Corning Toray Co., Ltd, was used.

Manufacturing Method

Step 1: Agitate and mix components 1, 2, 5, 6, 7, 8, 13, 14, and 15.

Step 2: Knead and mix components 3, 4, and 9 to 12 using a three-roller mill.

Step 3: Add the mixture obtained in step 2 to the mixture obtained in step 1 while agitating. Agitate and mix further.

Step 4: Add an aqueous phase in which components 16 to 21 are uniformly dissolved to the mixture obtained in Step 3 and emulsify. Fill a container with the emulsion to obtain the product.

When used, the obtained W/O type liquid foundation had superior emulsion stability and superior moisture resistance and cosmetic durability. Skin imperfections and wrinkles were concealed, tactile sensation was light, and bonding was superior.

Formulation Example 3: Liquid foundation (O/W type)

| Components | | |
|---|---|---|
| 1. | Carboxydecyltrisiloxane | 1 part |
| 2. | Polysorbate 80 | 1.2 parts |
| 3. | Sorbitan sesquioleate | 0.2 parts |
| 4. | Glyceryl stearate | 1.5 parts |
| 5. | Behenyl alcohol | 2.5 parts |
| 6. | Cyclopentasiloxane | 8 parts |
| 7. | Dimethicone (6 cs) | 3 parts |
| 8. | Squalane | 3 parts |
| 9. | Isotridecyl isononanoate | 3 parts |
| 10. | Glyceryl tricaprinate/tricaprylate | 3 parts |
| 11. | Co-modified organopolysiloxane P3 | 0.2 parts |
| 12. | Silicone treated titanium oxide | 8.5 parts |
| 13. | Silicone treated red iron oxide | 0.4 parts |
| 14. | Silicone treated yellow iron oxide | 1 part |
| 15. | Silicone treated black iron oxide | 0.1 parts |
| 16. | 1,3-butylene glycol | 8 parts |
| 17. | Sodium hydroxide aqueous solution (1%) | 15 parts |
| 18. | Carbomer (2%) | 10 parts |
| 19. | Purified water | Remainder |

Manufacturing Method

Step 1: Agitate and mix components 1 to 5 and 7 to 10.

Step 2: Knead and mix component 6 and 11 to 15 using a three-roller mill.

Step 3: Add the mixture obtained in step 2 to the mixture obtained in step 1 while agitating. Agitate and mix further.

Step 4: Add an aqueous phase in which components 16 to 19 are uniformly dissolved to the mixture obtained in Step 3 and emulsify. Fill a container with the emulsion to obtain the product.

When used, the obtained O/W type liquid foundation had superior emulsion stability and superior moisture resistance and cosmetic durability. Skin imperfections and wrinkles were concealed and spreadability and adhesion was superior.

Formulation Example 4: Sunscreen cream (W/O type)

| Components | | |
|---|---|---|
| 1. | Dimethicone (6 cs) | 3.8 parts |
| 2. | Cyclopentasiloxane | 6.7 parts |
| 3. | Isotridecyl isononanoate | 4 parts |
| 4. | Polyether-modified silicone (see note 1) | 2 parts |
| 5. | Cyclopentasiloxane, crosslinking polyether-modified silicone (see note 2) | 2.5 parts |
| 6. | Cyclopentasiloxane, dimethicone crosspolymer (see note 3) | 1.5 parts |
| 7. | Organo-modified bentonite | 0.2 parts |
| 8. | Silicone treated microparticle zinc oxide dispersion (zinc oxide: 60 wt %) (see note 4) | 35 parts |
| 9. | Silicone treated fine particulate titanium oxide dispersion (titanium oxide: 40 wt %) (see note 5) | 25 parts |
| 10. | Copolymer of Cyclopentasiloxane and (acrylates/polytrimethylsiloxy methacrylate) (see note 6) | 3.3 parts |
| 11. | 1,3-butylene glycol | 2 parts |
| 12. | Sodium citrate | 0.2 parts |
| 13. | Sodium chloride | 0.5 parts |
| 14. | Purified water | Remainder |

Note 1:
ES-5612, manufactured by Dow Corning Toray Co., Ltd. was used.
Note 2:
DC-9011, manufactured by Dow Corning Toray Co., Ltd. was used.
Note 3:
DC-9040, manufactured by Dow Corning Toray Co., Ltd. was used.
Note 4:
Dispersion ZP3 described in the Practical Examples was used.
Note 5:
Dispersion TP3 described in the Practical Examples was used.
Note 6:
FA-4001CM, manufactured by Dow Corning Toray Co., Ltd. was used.

Manufacturing Method

Step 1: Mix components 1 to 10.

Step 2: Mix components 11 to 14.

Step 3: Add the aqueous phase obtained in Step 2 to the mixture obtained in Step 1 while agitating. After emulsifying, fill a container with the emulsion to obtain the product.

Formulation Example 3 is a sunscreen cream comprising a dispersion of an inorganic ultraviolet light blocking component treated using the co-modified polyorganosiloxane P3 according to the present invention. Although this sunscreen cream comprises a large amount of aqueous phase components and inorganic ultraviolet light blocking components, separation of the oil-based component and the powder does not occur and stability over time was superior, that is, the sunscreen cream could be stocked over an extended period of time at around 40° C. (ambient temperature during summer). Furthermore, when used, spreadability was excellent, stickiness was reduced and sensation during use was superior. The sunscreen cream was free of irritation, and long-lasting ultraviolet light protection effects were provided. There was no change in this excellent sensation during use from before storing at around 40° C. to after storing.

Formulation Example 4: Sunscreen (shaking type)

| Components | | |
|---|---|---|
| 1. | Octyl methoxycinnamate | 8 parts |
| 2. | Isotridecyl isononanoate | 7 parts |
| 3. | Diethylamino hydroxybenzoyl hexyl benzoate | 2 parts |
| 4. | Titanium oxide slurry (see note 1) | 5 parts |
| 5. | Zinc oxide slurry (see note 2) | 28 parts |
| 6. | Cyclopentasiloxane | 18.2 parts |
| 7. | Dimethicone crosspolymer | 3 parts |
| 8. | Trimethylsiloxysilicate | 3.3 parts |
| 9. | Preservative | 0.1 parts |
| 10. | Ethanol | 5 parts |
| 11. | 1,3-butylene glycol | 3 parts |
| 12. | Purified water | Remainder |

Note 1:
Dispersion ZP3 described in the Practical Examples was used.
Note 2:
Dispersion TP3 described in the Practical Examples was used.

Manufacturing Method

Step 1: Mix components 1 to 8.

Step 2: Add a mixture of components 9 to 12 to the mixture of Step 1 and emulsify.

The obtained sunscreen had reduced stickiness and superior sensation during use when applied on skin, and provided lasting ultraviolet light protection effects.

| Formulation Example 5: Base cream | | |
|---|---|---|
| Components | | |
| 1. | Dimethylpolysiloxane (2 $mm^2/s$) | 2 parts |
| 2. | Decamethyl cyclopentasiloxane | 10 parts |
| 3. | Polyether-modified silicone (see note 1) | 2 parts |
| 4. | Cetyl isooctanoate | 5 parts |
| 5. | Co-modified organopolysiloxane P3 | 0.5 parts |
| 6. | Paramethoxy cinnamic acid 2-ethylhexyl | 2 parts |
| 7. | Silicone elastomer (see note 2) | 4 parts |
| 8. | Silicone treated titanium oxide | 6 parts |
| 9. | Silicone treated red iron oxide | 0.3 parts |
| 10. | Silicone treated yellow iron oxide | 0.7 parts |
| 11. | Silicone treated black iron oxide | 0.07 parts |
| 12. | Organo-modified bentonite | 0.5 parts |
| 13. | Barium sulfate | 2 parts |
| 14. | Talc | 1 part |
| 15. | Nylon powder | 3 parts |
| 16. | Preservative | q.s. |
| 17. | Xanthan gum | 0.1 parts |
| 18. | L-ascorbic acid ester magnesium phosphate | 0.3 parts |
| 19. | Purified water | Remainder |

Note 1:
SS-2910 manufactured by Dow Corning Toray Co., Ltd. was used.
Note 2:
9045 Silicone Elastomer Blend, manufactured by Dow Corning was used.

Manufacturing Method

Step 1: Mix and disperse components 1 to 15.

Step 2: Mix components 16 to 18.

Step 3: Add the mixture obtained in Step 2 to the mixture obtained in Step 1 and emulsify at room temperature. Fill a container with the emulsion to obtain the product.

The base cream had excellent spreadability, superior uniformity of the cosmetic film, and had superior bonding to the skin. Additionally, skin imperfections, wrinkles, and pores were hardly noticeable. Moreover, the emulsion state of the base cream was stable.

| Formulation Example 6: Rouge | | |
|---|---|---|
| Components | | |
| 1. | Triethylhexanoin | 10.0 parts |
| 2. | Cetyl ethylhexanoate | 17.0 parts |
| 3. | Sorbitan sesquiisostearate | 4.0 parts |
| 4. | Microcrystalline wax | 10.0 parts |
| 5. | Paraffin wax | 15.0 parts |
| 6. | Diisostearyl malate | 7.0 parts |
| 7. | Glyceryl triisostearate | 9.0 parts |
| 8. | Propylene glycol dicaprate | 7.0 parts |
| 9. | Inulin stearate (Rheopearl ISK2, manufactured by Chiba Flour Milling Co., Ltd.) | 2.0 parts |
| 10. | Co-modified organopolysiloxane P7 | 3.0 parts |
| 11. | Copolymer of Isododecane and (acrylates/polytrimethylsiloxy methacrylate) (see note 1) | 3.0 parts |
| 12. | Dimethylpolysiloxane (100 cst) solution of trimethylsiloxysilicate (active component: 33%) | 2.0 parts |
| 13. | Yellow No. 4 | q.s. |
| 14. | Titanium oxide | 1.0 parts |
| 15. | Black iron oxide | 1.0 parts |
| 16. | Mica | 1.0 parts |
| 17. | Red 104 | q.s. |
| 18. | Purified water | 7.0 parts |
| 19. | 1,3-butylene glycol | 1.0 parts |
| 20. | Preservative | q.s. |
| 21. | Perfume | q.s. |

Note 1:
FA-4002ID, manufactured by Dow Corning Toray Co., Ltd. was used.

Manufacturing Method

Step 1: Heat and dissolve components 1 to 17.

Step 2: Mix components 18 to 20.

Step 3: Add the mixture of Step 2 to the mixture of Step 1 and further agitate and mix.

Step 4: Add component 21 to the mixture of Step 3. Fill a closed vessel with the obtained mixture to obtain the product.

The rouge had a luxurious feel and excellent spreadability; could be applied uniformly to the lips; and could deliver a finish having superior luster and feeling of sheerness. Furthermore, there was no stickiness on the lips after application, and storage stability in cases where the product was stocked was excellent.

| Formulation Example 7: Liquid rouge | | |
|---|---|---|
| Components | | |
| 1. | Copolymer of cyclopentasiloxane and (acrylates/polytrimethylsiloxy methacrylate) (see note 1) | 20 parts |
| 2. | Cyclopentasiloxane/trimethylsiloxysilicate (see note 2) | 25 parts |
| 3. | Aerosol-form silicic anhydride | 0.1 parts |
| 4. | Spherical urethane powder | 5 parts |
| 5. | Co-modified organopolysiloxane P7 | 5 parts |
| 6. | Octyl methoxy cinnamate | 1 part |
| 7. | Red No. 202 | 0.5 parts |
| 8. | Titanium oxide | 0.5 parts |
| 9. | Titanated mica | 3 parts |
| 10. | Perfume | 0.1 parts |
| 11. | Ethanol | 10 parts |
| 12. | Preservative | 0.2 parts |
| 13. | Sodium chloride | 0.1 parts |
| 14. | Purified water | 29.5 parts |

Note 1:
FA-4001CM, manufactured by Dow Corning Toray Co., Ltd. was used.
Note 2:
BY11-018, manufactured by Dow Corning Toray Co., Ltd. was used.

Manufacturing Method

A: Mix and disperse components 1 to 10.

B: Separately dissolve components 11 to 14 in a uniform manner.

C: Add B to A, emulsify, and degas. Then, fill a container with the obtained emulsion to obtain the water-in-oil emulsion rouge.

| Formulation 8: Lipstick | | |
|---|---|---|
| Components | | |
| 1. | Polyethylene-polypropylene copolymer | 5 parts |
| 2. | Candelilla wax | 5 parts |
| 3. | Carnauba wax | 5 parts |
| 4. | Vaseline | 10 parts |
| 5. | Cetyl 2-ethylhexanoate | 10 parts |
| 6. | Diglycerin diisostearate | 14.5 parts |
| 7. | Macademia nut oil | 7 parts |
| 8. | Inulin stearate (Rheopearl ISK2; manufactured by Chiba Flour Milling Co., Ltd.) | 23 parts |
| 9. | Co-modified organopolysiloxane P7 | 2 parts |
| 10. | Red No. 201 | 1 part |
| 11. | Red No. 202 | 3 parts |
| 12. | Yellow No. 4, aluminum lake | 3 parts |
| 13. | Titanium oxide | 1 part |
| 14. | Black iron oxide | 0.5 parts |
| 15. | Iron oxide titanated mica | 10 parts |
| 16. | Preservative | q.s. |
| 17. | Perfume | q.s. |

Manufacturing Method

A: Components 1 to 9 are heated and dissolved. Then, components 10 to 16 are added and mixed uniformly.

B: Component 17 is added to A, and a container is filled with the mixture. Thus, a lipstick is obtained.

Formulation Example 9: Lip gloss

| Components | | |
|---|---|---|
| 1. | Polyamide-modified silicone (see note 1) | 10 parts |
| 2. | Co-modified organopolysiloxane P3 | 1 part |
| 3. | Methylphenyl-modified silicone | 28 parts |
| 4. | Isodecyl isononanoate | 38 parts |
| 5. | Isohexadecane | 14 parts |
| 5. | Trioctanoin | 2 parts |
| 6. | Titanated mica | 3 parts |

Note 1:
2-8178 gellant, manufactured by Dow Corning, was used.

Manufacturing Method

Heat the components and then mix at 100° C. Then, fill a container with the mixture to obtain the product.

The lip gloss had good compatibility with oil-based raw materials and storage stability in cases where the product was stocked was excellent.

Formulation Example 10: Eye shadow

| Components | | |
|---|---|---|
| 1. | Dimethylpolysiloxane (2 cs) | 13 parts |
| 2. | Dimethylpolysiloxane (6 cs) | 12 parts |
| 3. | Co-modified organopolysiloxane P3 | 2 parts |
| 4. | PEG (10) lauryl ether | 0.5 parts |
| 5. | Octylsilane treated titanium oxide | 6.2 parts |
| 6. | Octylsilane treated sericite | 4 parts |
| 7. | Octylsilane treated mica | 6 parts |
| 8. | Sodium chloride | 2 parts |
| 9. | Propylene glycol | 8 parts |
| 10. | Preservative | q.s. |
| 11. | Perfume | q.s. |
| 12. | Purified water | bal. |

Manufacturing Method

A: Components 1 to 4 are mixed, and components 5 to 7 are added and dispersed uniformly.

B: Components 8 to 12 are dissolved uniformly.

C: B is added to A in small amounts and emulsified. Thus, an eye shadow is obtained.

The obtained eye shadow spread smoothly when applying and had superior color development.

Formulation Example 11: Mascara

| Components | | |
|---|---|---|
| 1. | Paraffin wax | 5 parts |
| 2. | Light liquid isoparaffin | Remainder |
| 3. | Capryl methicone | 0.5 parts |
| 4. | Co-modified organopolysiloxane P3 | 0.5 parts |
| 5. | Trioctanoin | 13 parts |
| 6. | Decamethyl cyclopentasiloxane | 20 parts |
| 7. | Inulin stearate | 5 parts |
| 8. | Cyclopentasiloxane, dimethicone crosspolymer (see note 1) | 10 parts |
| 9. | Fluorine compound surface coated black iron oxide | 6 parts |
| 10. | Sucrose fatty acid ester | 4 parts |
| 11. | Beeswax | 5 parts |
| 12. | Pentaerythritol rosinate | 5 parts |
| 13. | Preservative | q.s. |
| 14. | Purified water | 5 parts |

Note 1:
DC-9040, manufactured by Dow Corning was used

Manufacturing Method

Heat and dissolve components 1 to 12. Then, thoroughly mix and disperse. Add components 13 and 14 to the mixture and emulsify. Fill a container with the obtained emulsion to obtain the product.

The obtained mascara had a deep black color when applied and had superiorluster. Additionally, bonding to the eyelashes was excellent, curling and volumizing eyelash effects were superior, and durability of these effects was superior.

Products produced by replacing the components corresponding with silicone compounds Nos. 1 to 14 in the Formulation Examples of the cosmetic compositions recited in Patent Document 5 (WO2011/049248, filed by the present applicant) with the co-modified organopolysiloxanes (co-modified organopolysiloxanes P1 to P7) according to the present invention are included in the scope of the present invention as Formulation Examples of cosmetic compositions according to the present invention.

Specifically, examples of compositions recited in the Practical Examples and the like of Patent Document 5 where the co-modified organopolysiloxane according to the present invention can be used as a replacement component include emulsions, lip glosses, oil-based foundations, water-in-oil emulsion transparent anti-perspirant compositions, non-aqueous stick-form anti-perspirant compositions. Moreover, the following Formulation Examples are recited in paragraphs 0459 to 0501 of Patent Document 5.

Example 1: Emulsion foundation
Example 2: Liquid foundation
Example 3: Foundation
Example 4: Water-in-oil cream
Example 5: Water-in-oil emulsion composition
Example 6: Water-in-oil emulsion rouge (liquid)
Example 7: Liquid rouge
Example 8: Rouge
Example 9: Sunscreen emulsion
Example 10: Emulsion
Example 11: UV blocking cream
Example 12: UV blocking water-in-oil emulsion
Example 13: Sunscreen agent
Example 14: Water-in-oil emulsion sunscreen
Example 15: O/W cream
Example 16: Eye shadow
Example 17: Mascara
Example 18: Mascara
Example 19: Solid powder eye shadow
Example 20: Pressed powder cosmetic
Example 21: Powder foundation
Example 22: Pressed foundation
Example 23: Cream
Example 24: Foundation
Example 25: Water-in-oil emulsion-type sunscreen
Example 26: Lipstick
Example 27: Rouge
Example 28: Foundation Example 29: Anti-perspirant aerosolized cosmetic composition
Example 30: Nonaqueous pressurized anti-perspirant product
Example 31: Aerosol type anti-perspirant composition
Example 32: Anti-perspirant lotion composition
Example 33: W/O emulsion-type skin external use preparation
Example 34: Nonaqueous anti-perspirant deodorant stick composition
Example 35: W/O solid anti-perspirant stick composition
Example 36: W/O emulsion type anti-perspirant cream composition
Example 37: Mascara
Example 38: Aftershave cream
Example 39: Solid foundation
Example 40: Daytime use skin-lightening cream
Example 41: Sun tanning cream
Example 42: Polyol/O-type nonaqueous emulsion skin external use preparation
Example 43: Polyol/O-type nonaqueous emulsion skin external use preparation

INDUSTRIAL APPLICABILITY

The co-modified organopolysiloxane according to the present invention has low viscosity, low HLB, and superior surface treating properties and surface activity properties and, therefore, can be used in external use preparations, and particularly for industrial applications other than cosmetic compositions. Examples thereof include varnishes or coating additives having superior heat resistance, weather resistance, or electrical properties; foam stabilizers or modifying agents for polyol base compounds used in various urethane and foam materials; debonding agents or release agents; antifoaming agents; grease or oil compounds; modifying agents, additives, or surface treatment agents use for oil, rubber, or resin of insulating, glazing, water repelling, heating mediums, cooling mediums, and lubricants; compounds, modifying agents, and precursors for silane coupling agents; coating materials or sealing materials for buildings or linings; protective agents, lubricants, or buffer agents for fiber optics and electrical wiring; and the like. However, the novel organopolysiloxane copolymer according to the present invention is not limited to such applications.

The invention claimed is:

1. A co-modified organopolysiloxane having a viscosity at 25° C. of 200 to 1,300 mPa·s, a group that has a siloxane dendron structure, a hydrophilic group, and expressed by the following structural formula (1-1-1):

(1-1-1)

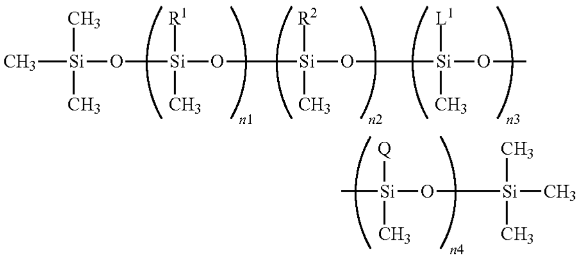

wherein, $R^1$ is a substituted or unsubstituted monovalent hydrocarbon group having from 1 to 30 carbons, or a hydrogen atom;

$R^2$ is a substituted or unsubstituted straight or branched monovalent hydrocarbon group having from 6 to 30 carbons; $L^1$ is a silylalkyl group having a siloxane dendron structure expressed by the following general formula (2) when i=1; and Q is a hydrophilic segment, (n1+n2+n3+n4) is a number in a range from 10 to 75, n1 is a number in a range from 0 to 70, n2 is a number in a range from 0 to 15, n3 is a number in a range from 1 to 10, and n4 is a number in a range from 0.3 to 1.5, wherein General Formula (2) is represented by:

(2)

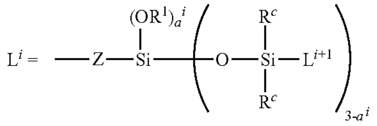

wherein, $R^1$ is as defined above, $R^C$ is an alkyl group having 1 to 6 carbons or a phenyl group, and Z is a divalent organic group; i represents a generation of the silylalkyl group represented by $L^i$, and is an integer of 1 to c when c is a number of generations that is a number of repetitions of the silylalkyl group; the number of generations c is an integer from 1 to 10, and $L^{i+1}$ is the silylalkyl group when i is less than c and is a methyl group or a phenyl group when i=c; and $a^i$ is a number in a range of 0 to 3; and a, b, c, and d are numbers in ranges so that $1.0 \leq a+b \leq 2.5$, $0.001 \leq c \leq 1.5$, and $0.001 \leq d \leq 1.5$, and wherein an HLB value calculated by formula (A) below is from 0.1 to 2.0:

HLB=(total molecular weight of hydrophilic group moiety/total molecular weight)×20 formula (A).

2. The co-modified organopolysiloxane according to claim 1, wherein in the formula (1-1-1), $L^1$ is a functional group expressed by general formula (2-1) or general formula (2-2) below:

General Formula (2-1)

(2-1)

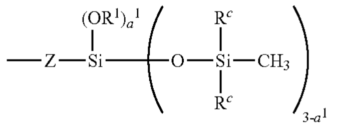

General Formula (2-2)

(2-2)

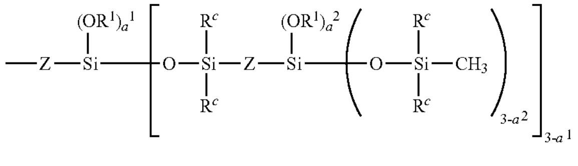

wherein $R^1$, $R^C$, and Z are as defined above, and $a^1$ and $a^2$ are each independently numbers in a range of 0 to 3.

3. The co-modified organopolysiloxane according to claim 1, wherein in the formula (1-1-1), Q is: a hydrophilic group that is bonded to the silicon atom via a linking group that is at least divalent, comprising a sugar alcohol represented by structural formulae (3-1) and (3-2) below, or a hydrophilic group that is bonded to the silicon atom via a linking group that is at least divalent, comprising at least one hydrophilic unit selected from hydrophilic units represented by structural formulae (3-3) to (3-6) below:

Structural formulae (3-1) and (3-2):

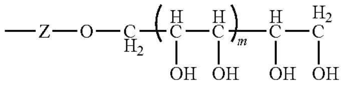
(3-1)

wherein Z is a divalent organic group, and m is 1 or 2;

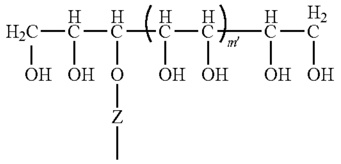
(3-2)

wherein Z is as defined above, and m' is 0 or 1;

Structural formulae (3-3) to (3-6):

$—C_rH_{2r}—O—$ (3-3)

wherein r is a number in a range of 1 to 6;

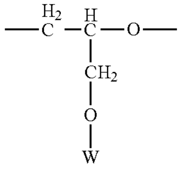
(3-4)

wherein W is a hydrogen atom or an alkyl group having from 1 to 20 carbons;

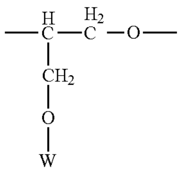
(3-5)

wherein W is as defined above; and

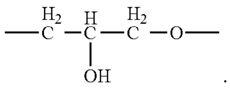
(3-6)

4. The co-modified organopolysiloxane according to claim 3, wherein in the structural formula (1-1-1), Q is a hydrophilic segment bonded to the silicon atom via a linking group that is at least divalent, comprising at least one linearly bonded hydrophilic unit selected from hydrophilic units represented by structural formulae (3-3) to (3-6); or Q is a hydrophilic group bonded to the silicon atom via a linking group that is at least divalent, comprising not less than two of at least one hydrophilic unit selected from hydrophilic units represented by structural formulae (3-3) to (3-6), and a branch unit selected from groups represented by structural formulae (3-7) to (3-9) below:

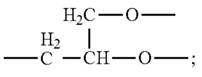
(3-7)

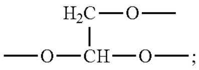
(3-8)

and

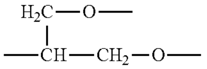
(3-9)

5. The co-modified organopolysiloxane according to claim 3, wherein in the structural formula (1-1-1), Q is a hydrophilic segment expressed by general formulae (4-1) to (4-4) below:

General Formula (4-1):

$—R^3(—O—X^1{}_m—R^4)_p$ (4-1)

wherein, $R^3$ is an organic group having (p+1) valency, and p is a number that is greater than or equal to 1 and less than or equal to 3; $X^1$ are each independently at least one hydrophilic unit selected from the hydrophilic units expressed by the general formulae (3-3) to (3-6) above, and m is a number in a range of 1 to 100; and $R^4$ is a hydrogen atom or a group selected from the group consisting of glycidyl groups, acyl groups, and alkyl groups having from 1 to 20 carbons;

General Formula (4-2):

$—R^3(—O—X^2)_p$ (4-2)

wherein, $R^3$ is as defined above, p is as defined above; and $X^2$ is a hydrophilic group represented by structural formula (4-2-1) below;

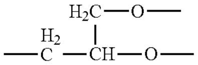
(4-2-1)

wherein, the at least one hydrophilic unit selected from the hydrophilic units expressed by the general formulae (3-3) to (3-6) is bonded to two oxygen atoms, each independently;

General Formula (4-3):

$—R^3(—O—X^3)_p$ (4-3)

wherein $R^3$ is as defined above, p is as defined above; and $X^3$ is a hydrophilic group represented by structural formula (4-3-1) below:

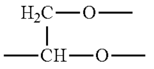
(4-3-1)

wherein, the at least one hydrophilic unit selected from the hydrophilic units expressed by the general formulae (3-3) to (3-6) is bonded to two oxygen atoms, each independently;

General Formula (4-4):

$$—R^3(—O—X^4)_p \quad (4\text{-}4)$$

wherein $R^3$ is as defined above, p is as defined above; and $X^4$ is a hydrophilic group represented by structural formula (4-4-1) below:

(4-4-1)

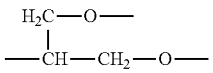

wherein, the at least one hydrophilic unit selected from the hydrophilic units expressed by the general formulae (3-3) to (3-6) is bonded to two oxygen atoms, each independently.

6. The co-modified organopolysiloxane according to claim 3, that is represented by structural formula (1-1-A) or (1-1-B) below:

-continued (3'-2)

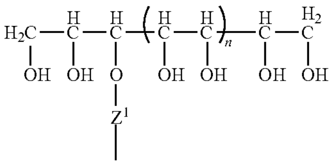

wherein $Z^1$ is a substituted or unsubstituted straight or branched alkylene group having from 3 to 5 carbons, and m is 1 or 2;

(4-1-2)

$$—R^3—(O—X^1{}_m—R^4)_p$$

(4-2-2)

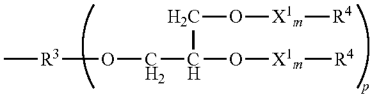

(1-1-A)

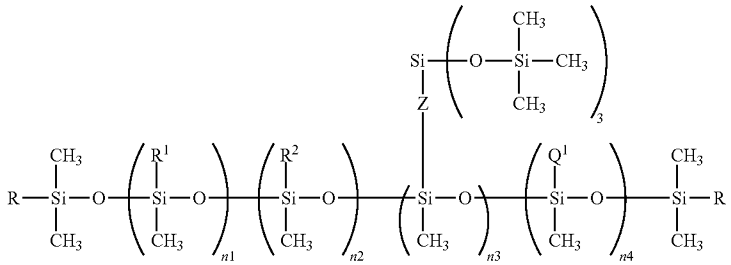

(1-1-B)

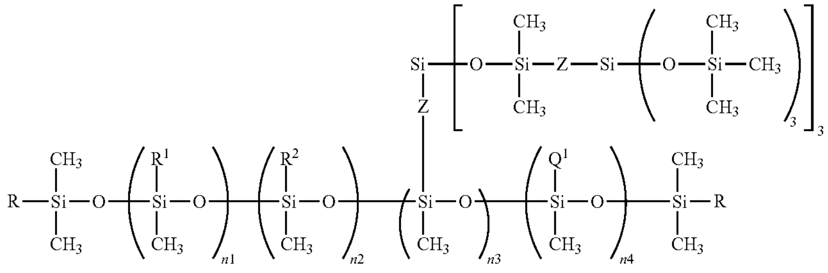

wherein Z, $R^1$, and $R^2$ are as defined above; R is a group selected from the $R^1$, $R^2$, and $L^1$ moieties, or $Q^1$; (n1+n2+n3+n4) is a number in a range from 10 to 75; n1 is a number in a range from 0 to 70, n2 is a number in a range from 0 to 15, n3 is a number in a range from 1 to 10, and n4 is a number in a range from 0.3 to 1.5; $Q^1$ are each independently a hydrophilic group selected from the group consisting of structural formulae (3'-1), (3'-2), (4-1-2), (4-2-2), (4-3-2), and (4-4-2) below:

(3'-1)

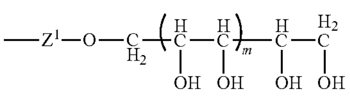

-continued (4-3-2)

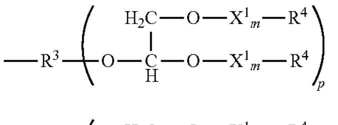

(4-4-2)

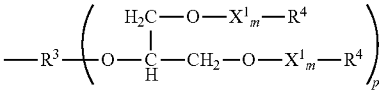

wherein $R^3$ is an organic group having (p+1) valency, and p is a number that is greater than or equal to 1 and less than or equal 3; X1 are each independently at least one hydrophilic unit selected from the hydrophilic units expressed by the general formulae (3-3) to (3-6), and m is a number in a range of 1 to 100; and R4 is a hydrogen atom or a group selected from the group consisting of glycidyl groups, acyl groups, and alkyl groups having from 1 to 20 carbons.

7. A surfactant or a surface treatment agent comprising the co-modified organopolysiloxane according to claim 1.

8. A powder treatment agent comprising the co-modified organopolysiloxane according to claim 1.

9. A powder composition comprising:

(A) the co-modified organopolysiloxane according to claim 1, and (B) a powder or coloring agent.

10. The powder composition according to claim 9, wherein the component (B) is one or two or more selected from the group consisting of an inorganic pigment powder, an organic pigment powder, and a resin powder, and has an average diameter in a range of 1 nm to 20 μm.

11. A powder in oil dispersion comprising: (A) the co-modified organopolysiloxane according to claim 1, (B) a powder or coloring agent, and (C) one or more oil agent selected from a silicone oil, a nonpolar organic compound, and a low polarity organic compound that is liquid from 5° C. to 100° C.

12. A preparation for external use comprising the co-modified organopolysiloxane according to claim 1.

13. The preparation for external use according to claim 12 wherein the preparation is a cosmetic composition or a medicament.

14. A cosmetic composition comprising the powder composition described in claim 9.

15. A cosmetic composition comprising the powder in oil dispersion according to claim 11.

16. A make-up cosmetic composition comprising:

(A) the co-modified organopolysiloxane according to claim 1;

(B) a powder or coloring agent; and (C) a silicone oil, a nonpolar organic compound, or a low polarity organic compound that is liquid from 5° C. to 100° C.

* * * * *